(12) United States Patent
Otterbein et al.

(10) Patent No.: US 7,981,448 B2
(45) Date of Patent: Jul. 19, 2011

(54) METHODS OF TREATING NECROTIZING ENTEROCOLITIS

(75) Inventors: Leo E. Otterbein, New Kensington, PA (US); Brian Zuckerbraun, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 590 days.

(21) Appl. No.: 10/413,817

(22) Filed: Apr. 15, 2003

(65) Prior Publication Data
US 2004/0005367 A1 Jan. 8, 2004

Related U.S. Application Data

(60) Provisional application No. 60/372,599, filed on Apr. 15, 2002.

(51) Int. Cl.
*A61K 33/00* (2006.01)
*A61P 1/00* (2006.01)

(52) U.S. Cl. .................................................. 424/699

(58) Field of Classification Search .................. 424/699
See application file for complete search history.

(56) References Cited

U.S. PATENT DOCUMENTS

| | | | |
|---|---|---|---|
| 4,053,590 A | 10/1977 | Bonsen et al. | |
| 4,264,739 A | 4/1981 | Grabner et al. | |
| 4,923,817 A | 5/1990 | Mundt | |
| 5,084,380 A | 1/1992 | Carney | |
| 5,180,366 A | 1/1993 | Woods | |
| 5,240,912 A | 8/1993 | Todaro | |
| 5,293,875 A | 3/1994 | Stone | |
| 5,449,665 A | 9/1995 | Sollevi | |
| 5,476,764 A | 12/1995 | Bitensky | |
| 5,498,421 A | 3/1996 | Grinstaff et al. | |
| 5,632,162 A | 5/1997 | Billy | |
| 5,664,563 A | 9/1997 | Schroeder et al. | |
| 5,731,326 A | 3/1998 | Hart et al. | |
| 5,763,431 A | 6/1998 | Jackson | |
| 5,792,325 A | 8/1998 | Richardson, Jr. | |
| 5,882,674 A | 3/1999 | Herrmann et al. | |
| 5,885,621 A | 3/1999 | Head et al. | |
| 5,914,316 A | 6/1999 | Brown et al. | |
| 6,066,333 A | 5/2000 | Willis et al. | |
| 6,069,132 A | 5/2000 | Revanker et al. | |
| 6,203,991 B1 | 3/2001 | Nabel et al. | |
| 6,313,144 B1 | 11/2001 | McCullough et al. | |
| 6,316,403 B1 | 11/2001 | Pinsky et al. | |
| 7,045,140 B2 | 5/2006 | Motterlini et al. | |
| 7,238,469 B2 | 7/2007 | Bach et al. | |
| 7,364,757 B2 | 4/2008 | Otterbein et al. | |
| 7,678,390 B2 | 3/2010 | Choi et al. | |
| 7,687,079 B2 | 3/2010 | Otterbein et al. | |
| 7,691,416 B2 | 4/2010 | Otterbein et al. | |
| 2002/0155166 A1 | 10/2002 | Choi et al. | |
| 2003/0009127 A1 | 1/2003 | Trescony et al. | |
| 2003/0039638 A1 | 2/2003 | Bach et al. | |
| 2003/0064114 A1 | 4/2003 | Motterlini et al. | |
| 2003/0068387 A1 | 4/2003 | Buelow et al. | |
| 2003/0219496 A1 | 11/2003 | Otterbein et al. | |
| 2003/0219497 A1 | 11/2003 | Otterbein et al. | |
| 2004/0052866 A1 | 3/2004 | Otterbein et al. | |
| 2004/0067261 A1 | 4/2004 | Haas et al. | |
| 2004/0131703 A1 | 7/2004 | Bach et al. | |
| 2004/0197271 A1 | 10/2004 | Kunka et al. | |
| 2004/0228930 A1 | 11/2004 | Billiar et al. | |
| 2004/0258772 A1 | 12/2004 | Otterbein et al. | |
| 2005/0048133 A1 | 3/2005 | Pinsky et al. | |
| 2005/0215468 A1 | 9/2005 | Bar-Or et al. | |
| 2005/0250688 A1 | 11/2005 | Pinsky et al. | |
| 2005/0255178 A1 | 11/2005 | Bloch et al. | |
| 2006/0003922 A1 | 1/2006 | Bach et al. | |
| 2007/0202083 A1 | 8/2007 | Bach et al. | |

FOREIGN PATENT DOCUMENTS

| | | |
|---|---|---|
| FR | 2 816 212 | 5/2002 |
| JP | 56079957 A | 6/1981 |
| WO | WO 94/22482 | 10/1994 |
| WO | WO 95/35105 | 12/1995 |
| WO | WO 98/08523 | 3/1998 |
| WO | WO 98/13058 | 4/1998 |
| WO | WO 99/49880 | 4/1999 |
| WO | WO 99/47512 | 9/1999 |
| WO | WO 02/09731 | 2/2002 |
| WO | WO 02/078684 | 10/2002 |
| WO | WO 02/092075 | 11/2002 |
| WO | WO 03/000114 | 1/2003 |
| WO | WO 03/066067 | 8/2003 |
| WO | WO 03/072024 | 9/2003 |
| WO | WO 03/088923 | 10/2003 |
| WO | WO 03/088981 | 10/2003 |
| WO | WO 03/094932 | 11/2003 |
| WO | WO 03/096977 | 11/2003 |
| WO | WO 03/103585 | 12/2003 |
| WO | WO 04/000368 | 12/2003 |
| WO | WO 2004/004817 | 1/2004 |
| WO | WO 2004/043341 | 5/2004 |

OTHER PUBLICATIONS

Verran et al, Use of liver allografts from carbon monoxide poisoned carveric dononrs, Transplantation, vol. 62, No. 10, pp. 1514-1515.*
Wing-Gaia et al., International Journal of Sport Nutrition and Exercise Metabolism (2005), vol. 15, pp. 680-688.*
Verran et al., Use of liver allografts from carbon monoxide poisoned cadaveric donors, Transplantation (1996), vol. 62, No. 10, pp. 1514, 1515.*
Abidin et al., "The Combined Effect of Carbon Monoxide and Normobaric Hyperoxia on Animals", Kosmicheskaya Biologiya I Aviakosmicheskaya Meditsina 6: 63-67 (1978).
Arita et al., "Prevention of Primary Islet Isograft Nonfunction in Mice with Pravastatin," *Transplantation* 65:1429-33 (1998).
Arnush et al., "IL-1 Produced and Released Endogenously within Human Islets Inhibits β Cell Function," J. Clin Invest. 102:516-26 (1998).
Bach et al., "Accommodation of vascularized xenografts: Expression of "protective genes" by donor endothelial cells in a host Th2 cytokine environment," *Nature Med.* 3:196-204 (1997).
Berney et al., "Islet cell transplantation: the future?" *Langenbeck's Arch. Surg.* 385: 373-8 (2000).

(Continued)

*Primary Examiner* — Johann R Richter
*Assistant Examiner* — Frank I Choi
(74) *Attorney, Agent, or Firm* — Fish & Richardson P.C.

(57) ABSTRACT

The present invention relates to a method of treating necrotizing enterocolitis in a patient, which includes administering a pharmaceutical composition that includes carbon monoxide to the patient.

39 Claims, 8 Drawing Sheets

OTHER PUBLICATIONS

Bentley et al., "Successful Cardiac Transplantation with Methanol or Carbon Monoxide-Poisoned Donors," *Thorac Surg* 71(4):1194-7 (2001).

Brouard et al., "Carbon Monoxide Generated by Heme Oxygenase-1 Suppresses Endothelial Cell Apoptosis," *J Exp Med* 192(7):1015-25 (2000).

Brown et al., "In vivo binding of carbon monoxide to cytochrome *c* oxidase in rat brain", American Physiological Society, pp. 604-610 (1990).

Campbell, "Living At Very High Altitudes", *The Lancet* 1:370-373 (1930).

Campbell, "The Effect of Carbon Monoxide and Other Agents Upon the Rate of Tumour Growth", J Pathology & Bacteriology 35:379-394 (1932).

Campell, "Cancer of Skin and Increase in Incidence of Primary Tumours of Lung in Mice Exposed to Dust Obtained from Tarred Roads", *Brit. J Exper. Pathol.* XV(5):24, 289-294 (1934).

Cantrell et al., "Low-Dose Carbon Monoxide Does Not Reduce Vasoconstriction in Isolated Rat Lungs", *Experimental Lung Research* 22:21-32 (1996).

Cardell et al., "Bronchondilatation in vivo by carbon monoxide, a cyclic GMP related messenger", British J. of Pharmacology 124:1065-1068 (1998).

Carlsson et al., "Measurements of Oxygen Tension in Native and Transplanted Rat Pancreatic Islets," *Diabetes* 47:1027-32 (1998).

Carraway et al., "Induction of ferritin and heme oxygenase-1 by endotoxin in the lung", *Am J Physiol Lung Cell Mol Physiol* 275:L583-592 (1998).

Cecil Textbook of Medicine ($21^{st}$ Ed. 2000) 1:273-279, 357-372, 387-419, 425-427, 436-448, 466-475, 507-512, 1060-1074.

Cecil Textbook of Medicine ($21^{st}$ Ed. 2000) 2:1492-1499, 2042-2047, 2079-2081.

Chapman et al., "Exogenous Carbon Monoxide Attenuates Aeroallergen-induced Eosinophilic Inflammation in Mice", *J Respiratory Critical Care Med* 159(3):A218 (1999).

Chapman et al., "Carbon Monoxide Attenuates Aeroallergen-induced Inflammation in Mice", *Am. J. Physiol. Lung Cell Mol Physiol.* 281:L209-L216 (2001).

Choi et al., "Heme Oxygenase-1: Function, Regulation, and Implication of a Novel Stress-inducible Protein in Oxidant-induced Lung Injury", *Am. J. Respir. Cell Mol. Biol.* 15:9-19 (1996).

Christodoulides et al., "Vascular Smooth Muscle Cell Heme Oxygenases Generate Guanylyl Cyclase-Stimulatory Carbon Monoxide," *Circulation* 97:2306-9 (1995).

Corbett et al., "Nitric oxide mediates cytokine-induced inhibition of insulin secretion by human islets of Langerhans," *Proc. Natl. Acad. Sci USA* 90:1731-5 (1993).

Davidson et al., "Inflammatory Modulation and Wound Repair"*J Investigative Dermatology* xi-xii (2003).

Dioum et al., "NPAS2: A Gas-Responsive Transcription Factor", Sciencexpress/www.sciencexpress.org/21 November 2002/pages 1-6/10.1126/science.1078456.

Donnelly et al., "Expression of Heme-Oxygenase in Human Airway Primary Epithelial Cells", *J Respiratory Critical Care Med* 159(3):A218 (1999).

Friebe et al., "YC-1 Potentiates Nitic Oxide- and Carbon Monoxide-Induced Cyclic GMP Effects in Human Platelets", Molecular Pharmacology 54: 962-967 (1998).

Gaine et al., "Induction of Heme Oxygenase-1 with Hemoglobin Depresses Vasoreactivity in Rat Aorta," *J Vasc Res* 36(2):114-9 (1999).

Grau et al., "Influence of Carboxyhemoglobin Level on Tumor Growth, Blood Flow, and Radiation Response in an Experimental Model," *Int. J. Radiation Oncology Biol. Phys.* 22:421-424 (1992).

Grau et al., "Effect of Carbon Monoxide Breathing on Hypoxia and Radiation Response in the SCCVII Tumor in vivo", *Int. J. Radiation Oncology Biol. Phys.* 29:449-454 (1994).

Hantson et al., "Organ Transplantation From Victims of Carbon Monoxide Poisoning," *Ann Emerg Med* 27(5):673-4 (1996).

Hebert et al., "Transplantation of Kidneys from a Donor with Carbon Monoxide Poisoning," New Engl J Med 326(23):1571 (1992).

Iberer et al., "Cardiac Allograft Harvesting after Carbon Monoxide Poisoning. Report of a Sucessful Orthotopic Heart Transplantation," *J Heart Lung Transplant* 12(3):499-500 (1993).

Katori et al., "Heme Oxygenase-1 System in Organ Transplantation", *Transplantation* 74(7):905-912 (2002).

Kaufman et al., "Differential Roles of Mac-$1^+$ Cells, and $CD4^+$ and $CD8^+$ T Lymphocytes in Primary Nonfunction and Classic Rejection of Islet Allografts,"*J Exp Med.* 172:291-302 (1990).

Koerner et al., "Extended Donor Criteria: Use of Cardiac Allografts after Carbon Monoxide Poisoning," *Transplantation* 63(9):1358-60 (1997).

Lacy et al., "Transplantation of Pancreatic Islets," *Ann. Rev. Immunol* 2:183-98 (1984).

Lee et al., "Regulation of Heme Oxygenase-1 Expression In Vivo and In Vitro in Hyperoxic Lung Injury", *Am. J. Respir. Cell Biol.* 14:556-568 (1996).

Lefer et al., "A Comparison of Vascular Biological Actions of Carbon Monoxide and Nitric Oxide", *Meth Find Exp Clin Pharmacol* 15(9):617-622 (1993).

Leikin et al., "The Toxic Patient as a Potential Organ Donor," *Am J Emerg Med* 12(2):151-4 (1994).

Mandrup-Poulsen et al., "Human Tumor Necrosis Factor Potentiates Human Interleukin 1-Mediated Rat Pancreatic β-Cell Cytotoxicity," *J. Immunol* 139:4077-82 (1987).

Mansouri et al., "Alteration of Platelet Aggregation by Cigarette Smoke and Carbon Monoxide," *Thromb Haemost* 48:286-8 (1982).

Maxwell et al., "Studies in Cancer Chemotherapy: XI The Effect of CO, HCN, and Pituitrin Upon Tumor Growth", Dept. of Cancer Research, Santa Barbara Cottage Hospital, pp. 270-282 (Jan. 30, 1933).

Meilin et al., Effects of carbon monoxide on the brain may be mediated by nitric oxide, *J Appl Physiol.* 81(3):1078-83 (1996).

The Merck Manual ($16^{th}$ Ed. 1992) pp. 646-657.

Minamino et al., "Targeted expression of heme oxygenase-1 prevents the pulmonary inflammatory and vascular response to hypoxia", *PNAS* 98(15):8798-8803 (2001).

Myers, "Cirrhotic cardiomyopathy and liver transplantation," *Liver Transpl* 6(4 Suppl 1):S44-52 (2000).

Nagata et al.,"Destruction of Islet Isografts by Severe Nonspecific Inflammation," *Transplant Proc.* 22:855-6 (1990).

The New Encyclopedia Britannica ($15^{th}$ ed. 1994) vol. 26, *Macropaedia*, p. 756.

Otterbein et al., "Mechanism of hemoglobin-induced protection against endotoxemia in rats: a ferritin-independent pathway", *Am J Physiol Lung Cell Mol Physiol* 272:L268-275 (1997).

Otterbein et al., "Carbon monoxide has anti-inflammatory effects involving the mitogen-activated protein kinase pathway", *Nature Medicine* 6(4): 422-8 (2000).

Otterbein et al., "Carbon monoxide provides protection against hyperoxic lung injury", *The American Physiological Society* L688-L694 (1999).

Otterbein et al., "Carbon monoxide provides protection against hyperoxic lung injury in rats", *J Respiratory Critical Care Med* 159(3):A218 (1999).

Paredi et al., "Increased Carbon Monoxide in Exhaled Air of Cystic Fibrosis Patients", *J Respiratory Critical Care Med* 159(3):A218 (1999).

Petrache et al., "Heme oxygenase-1 inhibits TNF-α-induced apoptosis in cultured fibroblasts," *Am. J. Physiol. Lung Cell Mol. Physiol.* 287: L312-L319 (2000).

Piantadosi et al., "Production of Hydroxyl Radical in the Hippocampus After CO Hypoxia Hypoxia in the Rat", *Free Radical Biol. & Med.* 22(4):725-732 (1997).

Pozzoli et al., "Carbon Monoxide as a Novel Neuroendocrine Modulator: Inhibition of Stimulated Corticotropin-Releasing Hormone Release from Acute Rat Hypothalamic Explants," *Endocrinology* 135:2314-2317 (1994).

Rabinovitch et al., "Transfection of Human Pancreatic Islets With an Anti-Apoptotic Gene (*bcl-2*) Protects β-Cells From Cytokine-Induced Destruction," *Diabetes* 48:1223-9, 1999.

Ringel et al., "Carbon Monoxide-induced Parkinsonism", J. neurol. Sci. 16:245-251 (1972).

Roberts et al., "Successful Heart Transplantation From a Victim of Carbon Monoxide Poisoning," *Ann Emerg Med* 26(5):652-5 (1995).

Sato et al., "Carbon Monoxide Generated by Heme Oxygenase-1 Suppresses the Rejection of Mouse-to-Rat Cardiac Transplants," *J. Immunol.* 166: 4185-4194 (2001).

Schipper et al., "Expression of Heme Oxygenase-1 in the Senescent and Alzheimer-diseased Brain", *Annals of Neurology* 37(6): 758-68 (1995).

Shapiro et al., "Islet Transplantation in Seven Patients with Type 1 Diabetes Mellitus Using a Glucocorticoid-Free Immunosuppressive Regimen," *N. Engl. J. Med.*, 343:230-8, 2000.

Shennib et al., "Successful transplantation of a lung allograft from a carbon monoxide-poisoning victim," *Heart Lung Transplant* 11(1 Pt 1): 68-71 (1992).

Singhal et al., "Effects of Normobaric Hyperoxia in a Rat Model of Focal Cerebral Ischemia-Reperfusion", *J Cerebral Blood Flow & Medicine* 22:861-868 (2002).

Siow et al., "Heme oxygenase-carbon monoxide signalling pathway in atherosclerosis: anti-atherogenic actions of bilirubin and carbon monoxide?", *Cardiovascular Research* 41:385-394 (1999).

Smith et al., "Successful Heart Transplantation with Cardiac Allografts Exposed to Carbon Monoxide Poisoning," *Heart Lung Transplant* 11(4 Pt. 1):698-700 (1992).

Soares et al., "Expression of heme oxygenase-1 can determine cardiac xenograft survival," *Nat Med.* 4(9):1073-1077 (1998).

Stephens et al., "Further Observations Regarding Carbon Monoxide Gas as an Important Factor in the Causation of Industrial Cancer", *Medical Press and Circular* 183:283-288 (1933).

Tamayo et al., "Carbon monoxide inhibits hypoxic pulmonary vasoconstriction in rats by a cGMP-independent mechanism", *Pflugers Arch.* 434(6):698-704 (1997).

Taylor, "Anti-TNF Therapy for Rheumatoid Arthritis and Other Inflammatory Diseases", *Molecular Biotechnology* 19:153-168 (2001).

Tenderich et al., "Hemodynamic follow-up of cardiac allografts from poisoned donors," *Transplantation* 66(9):1163-7 (1998).

Tenhunen et al., "The Enzymatic Conversion of Heme to Bilirubin by Microsomal Heme Oxygenase," *Proc Natl Acad Sci USA* 61:748-755 (1968).

Tulis et al., "Adenovirus-Mediated Heme Oxygenase-1 Gene Delivery Inhibits Injury-Induced Vascular Neointima Formation", *Circulation* 104:2710-2715 (2001).

Utz et al., "Carbon Monoxide Relaxes Ileal Smooth Muscle Through Activation of Guanylate Cyclase," *Biochem Pharmacol.* 47:1195-201, 1991.

Vassalli et al., "Inhibition of Hypoxic Pulmonary Vasoconstriction By Carbon Monoxide in Dogs", European Respiratory Journal, ERS Annual Congress, Geneva, Switzerland, Sep. 19-23 (1998).

Verma et al., "Carbon Monoxide: A Putative Neural Messenger," *Science* 259:381-384, 1993.

Verran et al., "Use of Liver Allografts from Carbon Monoxide Poisoned Cadaveric Donors," *Transplantation* 62(10):1514-5 (1996).

Wang et al., "Resurgence of carbon monoxide: an endogenous gaseous vasorelaxing factor", *Can. J. Physiol. Pharmacol.* 76:1-15 (1998).

Weir et al., "Scientific and Political Impediments to Successful Islet Transplantation," *Diabetes* 46:1247-56, 1997.

Weir et al., "Islet transplantation as a treatment for diabetes," *J. Am. Optom. Assoc.* 69:727-32, 2000.

Welty et al., "Hyperoxic Lung Injury is Potentiated by SPC-Promotor Driven Expression of an HO-1 Transgene in Mice", *J Respiratory Critical Care Med* 159(3):A218 (1999).

Weng et al., "Transpulmonary HO-1 Gene Delivery in Neonatal Mice", *J Respiratory Critical Care Med* 159(3):A218 (1999).

Yuan et al., "Evidence of increased endogenous carbon monoxide production in newborn rat endotoxicosis," *Chinese Medical Sciences Journal* (1997), vol. 12, No. 4, 212-215.

Baim and Grossman, "Treatment of Coronary Stenoses and Occlusions with Coronary Angioplasty," Harrison's Principles of Internal Medicine, 13th Ed., vol. 1, 193:986-87 (1994).

Choi, "Heme Oxygenase-1 Protects the Heart," Circulation Research 89:105-107 (2001).

Clayton et al., "Inhaled carbon monoxide and hyperoxic lung injury in rats," Am. J. Physiol. Lung Cell Mol. Physiol. 281:L949-57 (2001).

Fujita et al., "Paradoxical rescue from ischemic lung injury by inhaled carbon monoxide driven by derepression of fibrinolysis," Nature Medicine 7:598-604 (2001).

Hayes et al., "A Review of Modern Concepts of Healing of Cutaneous Wounds," J. Dermatol. Surg. Oncol. 3(2):188-93 (1977).

Kyokane et al., "Carbon Monoxide From Heme Catabolism Protects Against Hepatobiliary Dysfunction in Endotoxin-Treated Rat Liver," Gastroenterology 120:1227-40 (2001).

Lee et al., "Intestinal Motility and Absorption in Acute Carbon Monoxide Poisoning," Seoul J. Med. 15:95-105 (1974); English translation.

Libby and Pober, "Chronic Rejection," Immunity 14:387-97 (2001).

Moore et al., "Inhaled Carbon Monoxide Suppresses the Development of Postoperative Ileus in the Murine Small Intestine," Gastroenterology 124:377-91 (2003).

Moore et al., "Pre-treatment with Low Concentrations of Carbon Monoxide (250 TO 75 ppm) for 3 hr prior to Laparotomy Protects Against Postoperative Ileus," Digestive Disease Week abstracts and Itinerary Planner 2003: Abstract No. M1337 (2003).

Nachar at al., "Low-Dose Inhaled Carbon Monoxide Reduces Pulmonary Vascular Resistance During Acute Hypoxemia in Adult Sheep," High Altitude Medicine & Biology 2:377-385 (2001).

Nakao et al., "Immunomodulatory effects of inhaled carbon monoxide on rat syngeneic small bowel graft motility," Gut 52:1278-85 (2003).

Otterbein LE, Choi AMK, "Carbon monoxide at low concentrations causes growth arrest and modulates tumor growth in mice,"[Abstract], Am. J. Respir. Crit. Care Med. 163:A476 (2001).

Otterbein et al., "Carbon monoxide suppresses arteriosclerotic lesions associated with chronic graft rejection and with balloon injury," Nature Medicine 9:183-90 (2003).

Pannen et al., "Protective Role of Endogenous Carbon Monoxide in Hepatic Microcirculatory Dysfunction after Hemorrhagic Shock in Rats," J. Clin. Invest. 102:1220-1228 (1998).

Peek et al., "Extracorporeal Membrane Oxygenation for Adult Respiratory Failure," Chest 112(3)759-64 (1997).

Zuckerbraun et al., "Carbon monoxide attenuated the development of necrotizing enterocolitis in an animal model," Surgical Infection Society 3:83 (2002).

Choi et al., "'Therapeutic' carbon monoxide may be a reality soon," Am. J. Respir. Crit. Care Med., 171(11):1318-1319 (2005).

Dolinay et al., "Can Inhalation Carbon Monoxide be utilized as a therapeutic modality in human diseases?", pp. 203-236 in Breath Analysis for Clinical Diagnosis and Therapeutic Monitoring, Amann and Smith, eds., World Scientific Publishing Company (2004).

Dolinay et al., "Inhaled carbon monoxide confers antiinflammatory effects against ventilator-induced lung injury," Am. J. Respir. Crit. Care Med. 170:613-20 (2004).

Favory et al., "Myocardial Dysfunction and Potential Cardiac Hypoxia in Rats Induced by Carbon Monxide Inhalation," Am. J. Respir. Crit. Care Med. 174:320-25 (2006).

Mayr et al., "Effects of carbon monoxide inhalation during experimental endotoxemia in humans," Am. J. Respir. Crit. Care Med., 171:354-360 (2005).

Mazzola et al., "Carbon monoxide pretreatment prevents respiratory derangement and ameliorates hyperacute endotoxic shock in pigs," FASEB J. 19:2045-2047 (2005).

Ryter et al., "Therapeutic applications of carbon monoxide in lung disease," Curr. Opin. Pharmacol., 6:257-262 (2006).

Ryter et al., "Heme oxygenase-1/carbon monoxide: from basic science to therapeutic applications," Physiol. Rev. 86(2):583-650 (2006).

Thom et al, "'Therapeutic' Carbon Monoxide May Be Toxic," Am. J. Respir. Crit. Care Med., 171(11):1318 (2005).

Appel et al., "The pig as a source of Cardiac xenografts," J. Card. Surg. 16:345-56 (2001).

Bach, "Heme oxygenase-1 as a protective gene," Wien. Klin. Wochenschr. 114(Suppl):4:1-3 (2002).

Billiar, "The diverging roles of carbon monoxide and nitric oxide in resuscitated hemorrhagic shock," Crit. Care Med. 27:2842-3 (1999).

Bracho et al., "Carbon Monoxide Protects against Organ Injury in Hemorrhagic Shock/Resuscitation," Journal of Surgical Research, 107:270, (2002), Abstract.

Brouard et al., "Carbon monoxide generated by Heme Oxygenase-1 (HO-1) suppresses endothelial cell apoptosis via activation of the p38 mitogen activated protein kinase (MAPK) pathway," Acta Haematologica 103(Suppl 1):64, (2000), Abstract.

Brouard et al., "Heme oxygenase-1-derived carbon monoxide requires the activation of transcription factor NF-kappa B to protect endothelial cells from tumor necrosis factor-alpha-mediated apoptosis," J. Biol. Chem., 277(20):17950-17961, (2002).

Brouard et al., "Molecular mechanism underlying the anti-apoptotic effect of Heme oxygenase-1 derived carbon monoxide," Xenotransplantation, 8(Suppl 1): p. 22 (2001).

Calabrese et al., "Carbon Monoxide (CO) Prevents Apoptotic Events Related to Ischemia/Reperfusion (IR) Injury in an hDAF Pig-to-Primate Xenotransplantation Model," Xenotransplantation 10:488, (2003), Abstract.

Carbon Monoxide Poisoning—Symptoms; http://my.webmd.com/hw/home_health/aa7304.asp;retrieved Jul. 11, 2005.

Carbon Monoxide Poisoning—What Happens; http://my.webmd.com/hw/home_health/aa7326.asp;retrieved Jul. 11, 2005.

Chapman and Choi, "Exhaled monoxides as a pulmonary function test: use of exhaled nitric oxide and carbon monoxide," Clin. Chest Med. 22:817-836 (2001).

Chin et al., "Transcriptional regulation of the HO-1 gene in cultured macrophages exposed to model airborne particulate matter," Am. J. Physiol. Lung Cell. Mol. Physiol., 284(3):L473-L480, (2003).

Choi and Otterbein, "Emerging role of carbon monoxide in physiologic and pathophysiologic states," Antioxid. Redox Signal. 4:227-228 (2002).

Cozzi et al., "Donor Preconditioning with Carbon Monoxide (CO) in Pig-to-Primate Xenotransplantation," Xenotransplantation 10:528, (2003), Abstract.

Crapo et al., "Single-breath carbon monoxide diffusing capacity," Clin. Chest Med., 22:637-649, (2001).

Deng et al., "Carbon Monoxide Potentiates Cerulein-Induced Pancreatitis in Chronic Alcohol-Fed Rats," Gastroenterology, 124(4):A618-19, (2003), Abstract.

Dyck et al., "Carbon Monoxide (CO) Attenuates Lipopolysaccharide (LPS)-Induced Cytokine Expression of IL-6," Acta Haematologica 103(Suppl 1):64, (2000), Abstract.

Farrugia and Szurszewski, "Heme oxygenase, carbon monoxide, and interstitial cells of Cajal," Microsc. Res. Tech. 47:321-4, (1999).

Günther et al., "Carbon monoxide protects pancreatic beta-cells from apoptosis and improves islet function/survival after transplantation," Diabetes, 51(4):994-999, (2002).

Hartsfield and Choi, "Mitogen activated protein kinase (MAPK) is modulated by both endogenous and exogenous carbon monoxide," FASEB Journal 12:A187, 1088, (1998), Abstract.

Hartsfield et al., "Differential signaling pathways of HO-1 gene expression in pulmonary and systemic vascular cells," Am. J. Physiol., 277(6 Pt 1):L1133-L1141, (1999).

Hartsfield et al., "Regulation of heme oxygenase-1 gene expression in vascular smooth muscle cells by nitric oxide," Am. J. Physiol., 273(5 Pt 1):L980-988, (1997).

Hartsfield, "Targeted Overexpression of Heme Oxygenase-1 (HO-1) Attenuates Hypoxia-Induced Right Ventricular Hypertrophy," FASEB Journal 13:A827, (1999), Abstract.

Horvath et al., "Haemoxygenase-1 induction and exhaled markers of oxidative stress in lung diseases', summary of the ERS Research Seminar in Budapest, Hungary, Sep. 1999," Eur. Respir. J., 18(2):420-430, (2001).

Huizinga, Jan D., "Physiology and Pathophysiology of the Interstitial Cell of Cajal: From Bench to Bedside: II. Gastric motility: lessons from mutant mice on slow waves and innervation," Am. J. Physiol. 281:1129-1134, (2001).

Kozma et al, "Role of carbon monoxide in heme-induced vasodilation," Eur. J. Pharmacol., 323:R1-2 (1997).

Liu et al., "Carbon monoxide and nitric oxide suppress the hypoxic induction of vascular endothelial growth factor gene via the 5' enhancer," J. Biol. Chem. 273(24):15257-62 (1998).

Miller et al., "Heme oxygenase 2 is present in interstitial cell networks of the mouse small intestine," Gastroenterology 114:239-244 (1998).

Moore et al., "Carbon Monoxide Protects against Intestinal Dysmotility Associated with Small Bowel Transplantation," Gastroenterology 122:A38, (2002), Abstract.

Moore et al., "Carbon Monoxide Suppresses the Development of Ileus Associated with Surgical Manipulation of the Small Intestine," Gastroenterology 122:A61-A62, (2002), Abstract.

Mori et al., "Evaluation of hypothermic heart preservation with University of Wisconsin solution in heterotopically and orthotopically transplanted canine hearts," J. Heart Lung Transplant. 13:688-950 (1994).

Morse et al., "Carbon monoxide-dependent signaling," Crit. Care Med., 30:S12-S17, (2001).

Morse et al., "Suppression of inflammatory cytokine production by carbon monoxide involves the JNK pathway and AP-1," J. Biol. Chem., 278(39):36993-36998, (2003).

Nakao et al., "Protective effect of carbon monoxide inhalation for cold-preserved small intestinal grafts," Surgery 134(2):285-292 (2003).

Ning et al., "TGF-beta1 stimulates HO-1 via the p38 mitogen-activated protein kinase in A549 pulmonary epithelial cells," Am. J. Physiol. Lung Cell. Mol. Physiol., 283(5):L1094-L1102, (2002).

Otterbein et al., "Carbon monoxide at low concentrations induces growth arrest and modulates tumor growth in mice," Exp. Biol. Med., 228(5):633, (2003), Abstract.

Otterbein et al., "Carbon Monoxide Inhibits TNF α-Induced Apoptosis and Cell Growth in Mouse Fibroblasts," American Journal of Respiratory and Critical Care Medicine 159(3 Suppl.):A285 (1999).

Otterbein et al., "Carbon Monoxide Mediates Anti-Inflammatory Effects Via the P38 Mitogen Activated Protein Kinase Pathway," Acta Haematologica 103: 64, (2000), Abstract.

Otterbein et al., "Carbon Monoxide Modulates Lipolysaccharide (LPS)-Induced Inflammatory Responses in vivo and in vitro," American Journal of Respiratory and Critical Care Medicine 159(3 Suppl.):A481 (1999).

Otterbein et al., "Carbon Monoxide Protects Against Oxidant-Induced Lung Injury in Mice Via the p38 Mitogen Activated Protein Kinase Pathway," Acta Haematologica 103:83, (2000), Abstrac.

Otterbein et al., "Carbon Monoxide, A Gaseous Molecule with Anti-Inflammatory Properties," pp. 133-156 in Disease Markers in Exhaled Breath, Marczin et al., eds., Marcel Dekker, Inc., New York, (2003).

Otterbein et al., "Exogenous administration of heme oxygenase-1 by gene transfer provides protection against hyperoxia-induced lung injury," J. Clin. Invest., 103(7):1047-1054, (1999).

Otterbein et al., "Heme oxygenase: colors of defense against cellular stress," Am. J. Physiol. Lung Cell. Mol. Physiol., 279(6):L1029-L1037, (2000).

Otterbein et al., "Protective effects of heme oxygenase-1 in acute lung injury," Chest. 116:61S-63S, (1999).

Otterbein, "Anti-Inflammatory Effects of Carbon Monoxide in the Lung," CRISP Data Base National Institute of Health; Doc. No. CRISP/2003HL071797-01A1, (2003).

Otterbein, "Carbon monoxide: innovative anti-inflammatory properties of an age-old gas molecule," Antioxid. Redox Signal., 4:309-319, (2002).

Pileggi et al., "Heme oxygenase-1 induction in islet cells results in protection from apoptosis and improved in vivo function after transplantation," Diabetes, 50(9):1983-1991, (2001).

Ryter and Choi, "Heme Oxygenase-1: Molecular Mechanisms of Gene Expression in Oxygen-Related Stress," Antioxid. Redox Signal. 4:625-632, (2002).

Ryter et al., "Heme oxygenase/carbon monoxide signaling pathways: Regulation and functional significance," Mol. Cell. Biochem., 234-235(1-2):249-63, (2002).

Ryter et al., "Mitogen Activated Protein Kinase (MAPK) Pathway Regulates Heme Oxygenase-1 Gene Expression by Hypoxia in Vascular Cells," Exp. Biol. Med., 228(5):607, (2003), Abstract.

Sarady et al., "Carbon monoxide modulates endotoxin-induced production of granulocyte macrophage colony-stimulating factor in macrophages," Am. J. Respir. Cell. Mol. Biol., 27(6):739-745, (2002).

Sarady et al., "Cytoprotection by heme oxygenase/CO in the lung," in Disease Markers in Exhaled Breath, Marczin and Yacoub, eds., IOS Press, 346:73-78, (2002).

Sasidhar et al., "Exogenous Carbon Monoxide Attenuates Mitogen Activated Protein Kinase (MAPK) Activation in Rat Pulmonary Artery Endothelial Cells Exposed to Hypoxia," American Journal of Respiratory and Critical Care Medicine. 1999;159(3 Suppl.):A352.

Sass et al., "Heme Oxygenase-1 Induction Prevents Apoptotic Liver Damage in Mice," Naunyn-Schmiedeberg's Archives of Pharmacology 367:R78, (2003).

Sato et al., "Carbon monoxide can fully substitute Heme Oxygenase-1 in suppressing the rejection of mouse to rat cardiac transplants," Acta Haematologica, 103(Suppl. 1):87, Abstract 348 (2000).

Sato et al., "Heme oxygenase-1 or carbon monoxide prevents the inflammatory response associated with xenograft rejection," Acta Haematologica, 103(Suppl. 1):87, Abstract 345 (2000).

Sethi et al, "Differential modulation by exogenous carbon monoxide of TNF-alpha stimulated mitogen-activated protein kinases in rat pulmonary artery endothelial cells," Antioxid. Redox Signal., 4:241-8, (2002).

Sethi et al., "Differential Effects of Exogenous Carbon Monoxide on TNF-α-Induced Mitogen Activated Protein (MAP) Kinase Signaling Pathway in Rat Pulmonary Artery Endothelial Cells," American Journal of Respiratory and Critical Care Medicine 159(3 Suppl.):A350 (1999).

Seyfried et al., "HO-1 induction protects mice from Immune-mediated liver injury," Naunyn-Schmiedeberg's Archives of Pharmacology 367:R80 (2003).

Slebos et al., "Heme oxygenase-1 and carbon monoxide in pulmonary medicine," Respir Res. 4(7):1-13, (2003).

Soares et al, "Heme oxygenase-1, a protective gene that prevents the rejection of transplanted organs," Immunol. Rev. 184:275-85, (2001).

Soares et al, "Modulation of endothelial cell apoptosis by heme oxygenase-1-derived carbon monoxide," Antioxid. Redox Signal., 4:321-329, (2002).

Soares et al., "Heme Oxygenase-1 and/or Carbon Monoxide can Promote Organ Graft Survival," in Disease Markers in Exhaled Breath, Marczin and Yacoub, eds., IOS Press, 346:267-273, (2002).

Song et al., "Carbon monoxide induces cytoprotection in rat orthotopic lung transplantation via anti-inflammatory and anti-apoptotic effects," Am. J. Pathol., 163(1):231-242, (2003).

Song et al., "Carbon monoxide inhibits human airway smooth muscle cell proliferation via mitogen-activated protein kinase pathway," Am. J. Respir. Cell. Mol. Biol. 27(5):603-610, (2002).

Song et al., "Regulation of IL-1beta-induced GM-CSF production in human airway smooth muscle cells by carbon monoxide," Am. J. Physiol. Lung Cell. Mol. Physiol., 284(1):L50-L56, (2003).

Stupfel and Bouley, "Physiological and Biochemical Effects on Rats and Mice Exposed to Small Concentrations of Carbon Monoxide for Long Periods," Ann. N.Y. Acad. Sci. 174:343-368 (1970).

Suganuma et al., "A new process of cancer prevention mediated through inhibition of tumor necrosis factor alpha expression," Cancer Res. 56(16):3711-5 (1996).

Tobiasch et al, "Heme oxygenase-1 protects pancreatic β cells from apoptosis caused by various stimuli," J. Investig. Med., 49:566-71, (2001).

Toda et al., "Exogenous carbon monoxide protects endothelial cells against oxidant stress and improves graft function after lung transplantation," Circulation, 98(17):I265 (1998).

Yamashita et al., "Effects of HO-1 induction and carbon monoxide on cardiac transplantation in mice," Exp. Biol. Med., 228(5):616, (2003), Abstract.

Zhang et al., "Carbon monoxide inhibition of apoptosis during ischemia-reperfusion lung injury is dependent on the p38 mitogen-activated protein kinase pathway and involves caspase 3," J. Biol. Chem., 278(2):1248-1258, (2003).

Zhang et al., "Mitogen-activated protein kinases regulate HO-1 gene transcription after ischemia-reperfusion lung injury," Am. J. Physiol. Lung Cell. Mol. Physiol., 283(4):L815-L829, (2002).

Zhou et al., "Endogenous carbon monoxide and acute lung injury," Section of Respiratory System Foreign Medical Sciences 19:185-187 (1999) (English translation provided).

Zuckerbraun and Billiar, "Heme oxygenase-1: a cellular Hercules" Hepatology, 37(4):742-744, (2003).

Zuckerbraun et al., "Carbon monoxide inhibits intestinal inducible nitric oxide synthase production and ameliorates intestinal inflammation in experimental NEC," J. Amer. College of Surgeons 197:S50 (2003).

Zuckerbraun et al., "Carbon Monoxide Protects Hepatocytes from TNF-alpha/Actinomycin D Induced Cell Death," Critical Care Medicine 29:A59 (2001).

"Carbon Monoxide to Prevent Lung Inflammation," http://www.clinicaltrials.gov/ct/show/NCT00094406?order=2 (website visited by Applicant on Aug. 28, 2006).

"Modification of Chronic Inflammation by Inhaled Carbon Monoxide in Patients With Stable Chronic Obstructive Pulmonary Disease (COPD)," http://www.clinicaltrials.gov/ct/show/NCT00122694?order=1 (website visited by Applicant on Aug. 28, 2006).

Allred et al., "Effects of Carbon Monoxide on Myocardial Ischemia," Environmental Health Perspectives 91:89-132 (1991).

American Thoracic Society, "Single breath carbon monoxide diffusing capacity (transfer factor): recommendations for a standard technique," Am. Rev. Respir. Dis. 136:1299-1307 (1987).

American Thoracic Society, "Single breath carbon monoxide diffusing capacity (transfer factor): recommendations for a standard technique-1995 update," Am. J. Respir. Crit. Care. Med. 152:2185-2198 (1995).

Arcasoy et al., "Erythropoietin (EPO) Stimulates Angiogenesis In Vivo and Promotes Wound Healing," Blood 98:822A-823A, Abstract (2001).

Caplan et al., "Role of asphyxia and feeding in a neonatal rat model of necrotizing enterocolitis," Pediatr. Pathol. 14:1017-1028 (1994).

Czlonkowska et al., "Immune processes in the pathogenesis of Parkinson's disease—a potential role for microglia and nitric oxide," Med. Sci. Monit. 8:RA165-RA177 (2002).

Goldberg and Schneider, "Similarities between the oxygen-sensing mechanisms regulating the expression of vascular endothelial growth factor and erythropoietin," J. Biol. Chem. 269:4355-359 (1994).

Guo, "The Research Status of the Gas Messenger Molecules of Nitric Oxide and Carbon Monoxide in the Biomedicine Field," Practical Journal of Cardiac, Cerebral and Pulmonary Vascular Diseases vol. 8(2) (2000) (English translation included).

Harmey and Bouchier-Hayes, "Vascular endothelial growth factor (VEGF), a survival factor for tumour cells: implications for anti-angiogenic therapy," Bioessays 24:280-83 (2003).

Josko, "Vascular endothelial growth factor (VEGF) and its effect on angiogenesis," Medical Science Monitor 6:1047-52 (2000).

Krause et al., "Recombinant human erythropoietin and VEGF have equal angiogenic potency: Investigation in a novel in vitro assay of human vascular tissues," European Heart J. 22:154 Abstract (2001).

Omaye, "Metabolic modulation of carbon monoxide toxicity," Toxicol. 180:139-150 (2002).

Potter et al., "The inflammation-induced pathological chaperones ACT and apo-E are necessary catalysts of Alzheimer amyloid formation," Neurobiology of Aging 22:923-30 (2001).

Shahin et al., "Carboxyhemoglobin in pediatric sepsis and the systematic inflammatory response syndrome," Clinical Intensive Care 11(6):311-17 (2000).

Stewart, "The effect of carbon monoxide on humans," J. Occup. Med. 18:304-309 (1976).

Stewart, "The effects of low concentrations of carbon monoxide in man," Scand. J. Respir. Dis. Suppl. 91:56-62 (1974).

Thiemermann, "Inhaled CO: Deadly gas or novel therapeutic?" Nature Medicine 7(5): 534-35 (2001).

Vreman et al., "Carbon monoxide and carboxyhemoglobin," Adv. Pediatr. 42:303-34 (1995).

Wright and Shephard, "Physiological effects of carbon monoxide," Int. Rev. Physiol. 20:311-68 (1979).

Zegdi et al., "Increased endogenous carbon monoxide production in severe sepsis," Intensive Care Medicine 23:793-96 (2002).

Zuckerbraun et al., "Carbon Monoxide Protects against Liver Failure through Nitric Oxide-induced Heme Oxygenase 1," J. Exp. Med. 198:1707-716 (2003).

Bathoorn et al., "Effects of low dose inhaled carbon monoxide in patients with COPD," *Eur. Respir. J.*, 28(Suppl.50):661s (2006).

Mazzola et al., "Carbon monoxide pretreatment prevents respiratory derangement and ameliorates hyperacute endotoxic shock in pigs," *The FASEB Journal* [online], Oct. 13, 2005 [retrieved on Jun. 1, 2007]. Retrieved from the Internet:<URL:http://www.fasebj.org/cgi/doi/10.1096/fj.05-3782fje>.

Ellenhorn and Barceloux, "Carbon Monoxide" in *Medical Toxicology, Diagnosis and Treatment of Human Poisoning* (New York, New York) pp. 820-829 (1988).

Hartsfield, "Cross talk between carbon monoxide and nitric oxide," Antioxid. Redox Signal. 4:301-307 (2002).

Johnson et al., "Relationships between drug activity in NCI preclinical in vitro and in vivo models and early clinical trials," Br. J. Cancer 84:1424-31(2001).

Morse and Choi, "Heme oxygenase-1: from bench to bedside," Am. J. Respir. Crit. Care Med. 172:660-670 (2005).

Motterlini et al., "Carbon Monoxide-Releasing Molecules: Characterization of Biochemical and Vascular Activities," Circ. Res. 90:e17-24 (2002).

Nakao et al., "A single intraperitoneal dose of carbon monoxide-saturated ringer's lactate solution ameliorates postoperative ileus in mice," J. Pharrnacol. Exp. Ther. 319:1265-75 (2006).

Raman et al, "Inhaled carbon monoxide inhibits intimal hyperplasia and provides added benefit with nitric oxide," J. Vasc. Surg. 44:151-158 (2006).

Ramlawi et al., "Inhaled Carbon Monoxide Prevents Graft-Induced Intimal Hyperplasia in Swine," J. Surg. Res. 138:121-127 (2007).

Wang et al., "Carbon monoxide-induced vasorelaxation and the underlying mechanisms," Br. J. Pharmacol. 121:927-934 (1997).

Bathoorn et al., "Anti-inflammatory effects of inhaled carbon monoxide in patients with COPD: a pilot study," Eur. Respir. J. 0: 09031936.00163206v1 (Aug. 22, 2007).

Bartholomew, G.W. and M. Alexander, "Microbial metabolism of carbon monoxide in culture and in soil," *Appl. Environ. Microbiol.*, 37(5):932-937 (1979).

Bishop, G.A. et al., "Spontaneous acceptance of liver transplants in rodents: evidence that liver leucocytes induce recipient T-cell death by neglect," *Immunol. Cell Biol.*, 80(1):93-100 (2002).

Datta, R. and J.G. Zeikus, "Modulation of Acetone-Butanol-Ethanol Fermentation by Carbon Monoxide and Organic Acids," *Appl. Environ. Microbiol.*, 49(3):522-529 (1985).

Kanoria, S. et al., "A model to study total hepatic ischemia-reperfusion injury," *Transplant Proc.*, 36(9):2586-2589 (2004).

Medline Plus Medical Dictionary, definitions of organ, tissue and cell, accessed Oct. 9, 2007.

Soares et al., "Heme oxygenase-1: from biology to therapeutic potential," Trends Mol. Med., 15:50-56 (2009).

Zuckerbraun et al., "Carbon monoxide protects against the development of experimental necrotizing enterocolitis," Am. J. Physiol. Gastrointest. Liver Physiol., 289:G607-G613 (2005).

USPTO Final Office Action in U.S. Appl. No. 10/676,280, mailed Apr. 16, 2009, 17 pages.

USPTO Non-Final Office Action in U.S. Appl. No. 10/600,182, mailed Apr. 30, 2009, 10 pages.

USPTO Notice of Allowance in U.S. Appl. No. 10/371,666, mailed Oct. 20, 2009, 15 pages.

USPTO Notice of Allowance in U.S. Appl. No. 10/053,535, mailed Oct. 21, 2009, 20 pages.

"Chapter 5.5 Carbon Monoxide," in Guidelines for Air Quality, Second Edition, WHO Regional Office for Europe, Copenhagen, Denmark (2000).

Bauer et al., "Bench-to-bedside review: carbon monoxide-from mitochondrial poisoning to therapeutic use," Crit. Care, 13:220 (2009).

Laine et al., "Chronic rejection and late renal allograft dysfunction," Pediatr. Nephrol., 10:221-229 (1996).

Perrissoud et al, "Inhibiting or potentiating effects of flavonoids on carbon tetrachloride-induced toxicity in isolated rat hepatocytes," Arneimittelforschung, 36:1249-53 (1986).

\* cited by examiner

A.

B.

METHODS OF TREATING NECROTIZING ENTEROCOLITIS

CROSS-REFERENCE TO RELATED APPLICATIONS

This application claims priority to U.S. Provisional Application No. 60/372,599 filed Apr. 15, 2002, which is incorporated herein by reference in its entirety.

STATEMENT AS TO FEDERALLY SPONSORED RESEARCH

This invention was made with Government support under National Institutes of Health Grant Nos. HL55330, HL60234, and AI42365. The Government has certain rights in this invention.

TECHNICAL FIELD

This invention relates to the treatment of gastrointestinal disorders.

BACKGROUND

Carbon monoxide (CO) is recognized as an important signaling molecule (Verma et al., Science 259:381-384, 1993). It has also been suggested that CO acts as a neuronal messenger molecule in the brain (Id.) and as a neuro-endocrine modulator in the hypothalamus (Pozzoli et al., Endocrinology 735: 2314-2317, 1994). Like nitric oxide (NO), CO is a smooth muscle relaxant (Utz et al., Biochem Pharmacol. 47:195-201, 1991; Christodoulides et al., Circulation 97:2306-9, 1995) and inhibits platelet aggregation (Mansouri et al., Thromb Haemost. 48:286-8, 1982). Inhalation of low levels of CO has been shown to have anti-inflammatory effects in some models.

Necrotizing enterocolitis (NEC) is a disease of newborns characterized by gut barrier failure, intestinal necrosis, sepsis, and multi-system organ failure (see, e.g., Oxford Textbook of Surgery, Morris and Malt, Eds., Oxford University Press (1994)).

SUMMARY

The present invention is based, in part, on the discovery that administration of CO can protect against the development of NEC.

Accordingly, the present invention features a method of treating, preventing, or reducing the risk of necrotizing enterocolitis in a patient. The method includes identifying a patient suffering from or at risk for necrotizing enterocolitis and administering to the patient a pharmaceutical composition comprising an amount of CO effective to treat necrotizing enterocolitis in the patient. The method can include the further step of monitoring the patient's NEC condition and/or determining whether the patient's condition has improved or the risk of NEC has abated.

The pharmaceutical composition can be administered to the patient by any method known in the art for administering gases, liquids, and/or solids to patients, e.g., via inhalation, insufflation, infusion, injection, and/or ingestion. In one embodiment of the present invention, the pharmaceutical composition is administered to the patient by inhalation. In another embodiment, the pharmaceutical composition is administered to the patient orally. In still another embodiment, the pharmaceutical composition is administered directly to the abdominal cavity of the patient. In yet another embodiment, the pharmaceutical composition is administered by an extracorporeal membrane gas exchange device or an artificial lung.

The patient can be an infant, e.g., a full-term infant, a premature infant and/or an infant that exhibits low birth weight. The infant can be a newborn, or can be, e.g., up to one year old (for example, up to six months, four months, three months, or two months old). The infant can be less than six weeks old, e.g., less than four weeks old. The NEC can be the result of any of a number of factors, e.g., hypoxia, hypothermia, hypotension, hyperviscosity of the blood, and/or acidosis, and/or where the patient has received an exchange transfusion, at least one hyperosmolar feed, a packed cell transfusion, and/or an overdosage of calcium antagonists. Further, the NEC can result from a situation where the patient suffers from mesenteric ischaemia and/or bacterial infection of the bowel wall (see, e.g., Oxford Textbook of Surgery, Morris and Malt, Eds., Oxford University Press (1994)). Alternatively, the NEC can result from surgery, e.g., where the patient has undergone, is about to undergo, or is undergoing surgery. The pharmaceutical composition can be in any form, e.g., gaseous or liquid form.

The invention also features a method of treating or preventing necrotizing enterocolitis in a patient, which includes identifying a patient suffering from or at risk for necrotizing enterocolitis, providing a vessel containing a pressurized gas comprising CO gas, releasing the pressurized gas from the vessel to form an atmosphere comprising CO gas, and exposing the patient to the atmosphere, wherein the amount of CO in the atmosphere is sufficient to treat necrotizing enterocolitis in the patient.

In another aspect, the invention features a method of performing abdominal surgery on a patient (e.g., an infant), which includes identifying a patient in need of abdominal surgery, wherein necrotizing enterocolitis is a significant risk of the abdominal surgery; performing abdominal surgery on the patient, and before, during, or after the performing step, causing the patient to inhale an amount of CO gas sufficient to reduce the risk of necrotizing enterocolitis in the patient.

Also included in the invention is a method of treating necrotizing enterocolitis in a patient, which includes: (a) identifying a patient suffering from necrotizing enterocolitis; (b) performing surgery on the patient to resect an affected portion of the patient's bowel; and (c) administering to the patient a pharmaceutical composition comprising an amount of carbon monoxide effective to treat necrotizing enterocolitis in the patient after step (a) and before, during, or after step (b).

In another aspect, the invention provides a vessel comprising medical grade compressed CO gas. The vessel can bear a label indicating that the gas can be used to treat NEC in a patient, e.g., an infant. The CO gas can be in an admixture with nitrogen gas, with nitric oxide and nitrogen gas, or with an oxygen-containing gas. The CO gas can be present in the admixture at a concentration of at least about 0.025%, e.g., at least about 0.05%, 0.10%, 0.50%, 1.0%, 2.0%, 10%, 50%, or 90%.

In still another aspect, the invention provides a method of treating NEC in a patient, which includes identifying a patient suffering from or at risk for NEC and administering to the patient at least one of the following treatments in conjunction with treatment with CO: inducing HO-1 or ferritin in the patient; expressing recombinant HO-1 or ferritin in the patient; and administering a pharmaceutical composition comprising HO-1, bilirubin, biliverdin, ferritin, or apoferritin, iron, desferoxamine, or iron dextran to the patient. Also contemplated is use of CO and any of the above-listed agents in the preparation of a medicament for treatment or prevention of NEC.

Further, the invention provides a method of treating NEC in a patient, which includes identifying a patient suffering from or at risk for NEC and administering at least one of the following treatments in conjunction with treatment with CO: intravenous nutrition; intravenous hydration; antimicrobial agents; performing nasogastric decompression on the patient, performing surgery on the patient; and draining the patient's peritoneal cavity.

Also within the invention is the use of CO in the manufacture of a medicament for treatment or prevention of NEC. The medicament can be used in a method for treating NEC in a patient suffering from or at risk for NEC in accordance with the methods described herein. The medicament can be in any form described herein, e.g., a liquid or gaseous CO composition.

Unless otherwise defined, all technical and scientific terms used herein have the same meaning as commonly understood by one of ordinary skill in the art to which this invention belongs. Suitable methods and materials are described below, although methods and materials similar or equivalent to those described herein can be used in the practice or testing of the present invention. All publications, patent applications, patents, and other references mentioned herein are incorporated by reference in their entirety. In case of conflict, the present specification, including definitions, will control. The materials, methods, and examples are illustrative only and not intended to be limiting.

The details of one or more embodiments of the invention are set forth in the description below. Other features, objects, and advantages of the invention will be apparent from the description and the claims.

DETAILED DESCRIPTION

Figure 1A:
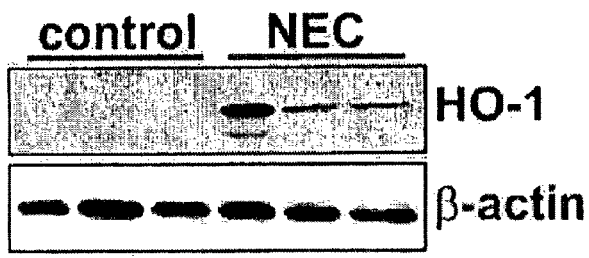
FIG. 1A is a picture of a Western blot illustrating that HO-1 expression is increased in intestinal samples from human neonates suffering from NEC (NEC) as compared to non-NEC patients (control) (n=3).

The term "carbon monoxide" (or "CO") as used herein describes molecular CO in its gaseous state, compressed into liquid form, or dissolved in aqueous solution. The terms "carbon monoxide composition" and "pharmaceutical composition comprising carbon monoxide" is used throughout the specification to describe a gaseous or liquid composition containing CO that can be administered to a patient and/or an organ, e.g., an organ affected by NEC. The skilled practitioner will recognize which form of the pharmaceutical composition, e.g., gaseous, liquid, or both gaseous and liquid forms, is preferred for a given application.

The terms "effective amount" and "effective to treat," as used herein, refer to an amount or concentration of CO utilized for period of time (including acute or chronic administration and periodic or continuous administration) that is effective within the context of its administration for causing an intended effect or physiological outcome in a patient. Effective amounts of CO for use in the present invention include, for example, amounts that reduce the symptoms of NEC in a patient, or improve the outcome.

For gases, effective amounts of CO generally fall within the range of about 0.0000001% to about 0.3% by weight, e.g., 0.0001% to about 0.25% by weight, preferably at least about 0.001%, e.g., at least 0.005%, 0.010%, 0.02%, 0.025%, 0.03%, 0.04%, 0.05%, 0.06%, 0.08%, 0.10%, 0.15%, 0.20%, 0.22%, or 0.24% by weight of CO. For liquid solutions of CO, effective amounts generally fall within the range of about 0.0001 to about 0.0044 g CO/100 g liquid, e.g., at least 0.0001, 0.0002, 0.0004, 0.0006, 0.0008, 0.0010, 0.0013, 0.0014, 0.0015, 0.0016, 0.0018, 0.0020, 0.0021, 0.0022, 0.0024, 0.0026, 0.0028, 0.0030, 0.0032, 0.0035, 0.0037, 0.0040, or 0.0042 g CO/100 g aqueous solution. Preferred ranges include, e.g., about 0.0010 to about 0.0030 g CO/100 g liquid, about 0.0015 to about 0.0026 g CO/100 g liquid, or about 0.0018 to about 0.0024 g CO/100 g liquid. A skilled practitioner will appreciate that amounts outside of these ranges may be used, depending upon the application.

The term "patient" is used throughout the specification to describe an animal, human or non-human, to whom treatment according to the methods of the present invention is provided. Veterinary applications are clearly contemplated by the present invention. The term includes but is not limited to mammals, e.g., humans, other primates, pigs, rodents such as mice and rats, rabbits, guinea pigs, hamsters, cows, horses, cats, dogs, sheep and goats. The term "treat(ment)," is used herein to describe delaying the onset of, inhibiting, or alleviating the effects of a condition, e.g., NEC, in a patient.

The term "necrotizing enterocolitis" or "NEC" is an art-recognized term and is used herein to refer to a disease of patients, particularly premature and newborn full term infants, that is characterized by gut barrier failure, intestinal necrosis, sepsis, and multi-system organ failure (*Oxford Textbook of Surgery*, Morris and Malt, Eds., Oxford University Press (1994)). NEC can affect any part of the bowel, e.g., the lower portion of the small intestine (ileum), the colon, and/or the upper small intestine. The risk of developing necrotizing enterocolitis is associated with many factors, e.g., low birth weight, hypoxia, hypothermia, hypotension, hyperviscosity, acidosis, or the presence of free oxygen radicals (Id.). Other risk factors include umbilical artery cannulae, exchange transfusion, hyperosmolar feeds, packed cell transfusion, or overdosage with calcium antagonists (Id.). Such factors may cause mesenteric ischaemia, which may allow bacterial infection of the bowel wall, resulting in necrosis of the infected tissue and/or perforation of the bowel wall and septicemia (Id.). NEC can also occur in newborns following surgery for gastrointestinal or other conditions (Id.).

Skilled practitioners will appreciate that a patient can be diagnosed as suffering from NEC by any method known in the art, e.g., by a physician's diagnosis (e.g., using imaging techniques such as ultrasonography, x-ray, and/or blood tests).

Individuals considered at risk for developing NEC may benefit particularly from the invention, primarily because prophylactic treatment can begin before there is any evidence of NEC. Individuals "at risk" include, e.g., premature and newborn infants, or individuals suffering from any of the conditions or having the risk factors described above. Skilled practitioners will appreciate that a patient can be diagnosed as being at risk for NEC by any method known in the art, e.g., by a physician's diagnosis (e.g., by a physician's assessment of a patient's risk factors).

Preparation of Gaseous Compositions

A CO composition may be a gaseous CO composition. Compressed or pressurized gas useful in the methods of the invention can be obtained from any commercial source, and in any type of vessel appropriate for storing compressed gas. For example, compressed or pressurized gases can be obtained from any source that supplies compressed gases, such as oxygen, for medical use. The term "medical grade" gas, as used herein, refers to gas suitable for administration to patients as defined herein. The pressurized gas including CO used in the methods of the present invention can be provided such that all gases of the desired final composition (e.g., CO, He, NO, $CO_2$, $O_2$, $N_2$) are in the same vessel, except that NO and $O_2$ cannot be stored together. Optionally, the methods of the present invention can be performed using multiple vessels containing individual gases. For example, a single vessel can be provided that contains CO, with or without other gases, the contents of which can be optionally mixed with room air or with the contents of other vessels, e.g., vessels containing oxygen, nitrogen, carbon dioxide, compressed air, or any other suitable gas or mixtures thereof.

Gaseous compositions administered to a patient according to the present invention typically contain 0% to about 79% by weight nitrogen, about 21% to about 100% by weight oxygen and about 0.0000001% to about 0.3% by weight (corresponding to about 1 ppb or 0.001 ppm to about 3,000 ppm) CO. Preferably, the amount of nitrogen in the gaseous composition is about 79% by weight, the amount of oxygen is about 21% by weight and the amount of CO is about 0.0001% to about 0.25% by weight. The amount of CO is preferably at least about 0.001%, e.g., at least about 0.005%, 0.010%, 0.02%, 0.025%, 0.03%, 0.04%, 0.05%, 0.06%, 0.08%, 0.10%, 0.15%, 0.20%, 0.22%, or 0.24% by weight. Preferred ranges include about 0.005% to about 0.24%, about 0.01% to about 0.22%, about 0.015% to about 0.20%, about 0.08% to about 0.20%, and about 0.025% to about 0.1% by weight. It is noted that gaseous CO compositions having concentrations of CO greater than 0.3% (such as 1% or greater) may be used for short periods (e.g., one or a few breaths), depending upon the application.

A gaseous CO composition may be used to create an atmosphere that comprises CO gas. An atmosphere that includes appropriate levels of CO gas can be created, for example, by providing a vessel containing a pressurized gas comprising CO gas, and releasing the pressurized gas from the vessel into a chamber or space to form an atmosphere that includes the CO gas inside the chamber or space. Alternatively, the gases can be released into an apparatus that culminates in a breathing mask or breathing tube, thereby creating an atmosphere comprising CO gas in the breathing mask or breathing tube, ensuring the patient is the only person in the room exposed to significant levels of CO.

CO levels in an atmosphere can be measured or monitored using any method known in the art. Such methods include electrochemical detection, gas chromatography, radioisotope counting, infrared absorption, colorimetry, and electrochemical methods based on selective membranes (see, e.g., Sunderman et al., Clin. Chem. 28:2026-2032, 1982; Ingi et al., Neuron 16:835-842, 1996). Sub-parts per million CO levels can be detected by, e.g., gas chromatography and radioisotope counting. Further, it is known in the art that CO levels in the sub-ppm range can be measured in biological tissue by a midinfrared gas sensor (see, e.g., Morimoto et al., Am. J. Physiol. Heart. Circ. Physiol 280:H482-H488, 2001). CO sensors and gas detection devices are widely available from many commercial sources.

Preparation of Liquid Compositions

A CO composition may also be a liquid CO composition. A liquid can be made into a CO composition by any method known in the art for causing gases to become dissolved in liquids. For example, the liquid can be placed in a so-called "$CO_2$ incubator" and exposed to a continuous flow of CO, preferably balanced with carbon dioxide, until a desired concentration of CO is reached in the liquid. As another example, CO gas can be "bubbled" directly into the liquid until the desired concentration of CO in the liquid is reached. The amount of CO that can be dissolved in a given aqueous solution increases with decreasing temperature. As still another example, an appropriate liquid may be passed through tubing that allows gas diffusion, where the tubing runs through an atmosphere comprising CO (e.g., utilizing a device such as an extracorporeal membrane oxygenator). The CO diffuses into the liquid to create a liquid CO composition.

It is likely that such a liquid composition intended to be introduced into a living animal will be at or about 37° C. at the time it is introduced into the animal.

The liquid can be any liquid known to those of skill in the art to be suitable for administration to patients (see, for example, Oxford Textbook of Surgery, Morris and Malt, Eds., Oxford University Press (1994)). In general, the liquid will be an aqueous solution. Examples of solutions include Phosphate Buffered Saline (PBS), Celsior™, Perfadex™, Collins solution, citrate solution, and University of Wisconsin (UW) solution (Oxford Textbook of Surgery, Morris and Malt, Eds., Oxford University Press (1994)). In one embodiment of the present invention, the liquid is Ringer's Solution, e.g., lactated Ringer's Solution, or any other liquid that can be used infused into a patient. In another embodiment, the liquid includes blood, e.g., whole blood.

Any suitable liquid can be saturated to a set concentration of CO via gas diffusers. Alternatively, pre-made solutions that have been quality controlled to contain set levels of CO can be used. Accurate control of dose can be achieved via measurements with a gas permeable, liquid impermeable membrane connected to a CO analyzer. Solutions can be saturated to desired effective concentrations and maintained at these levels.

Treatment of Patients with Carbon Monoxide Compositions

A patient can be treated with a CO composition by any method known in the art of administering gases and/or liquids to patients. CO compositions can be administered to a patient diagnosed with, or determined to be at risk for, NEC, e.g., newborns or premature infants. The present invention contemplates the systemic administration of liquid or gaseous CO compositions to patients (e.g., by inhalation and/or ingestion), and the topical administration of the compositions to the patient's gastrointestinal tract (e.g., by ingestion, insufflation, and/or introduction into the abdominal cavity).

Systemic Delivery of Carbon Monoxide

Gaseous CO compositions can be delivered systemically to a patient, e.g., a patient diagnosed with, or determined to be at risk for NEC. Gaseous CO compositions are typically administered by inhalation through the mouth or nasal passages to the lungs, where the CO is readily absorbed into the patient's bloodstream. The concentration of active compound (CO) utilized in the therapeutic gaseous composition will depend on absorption, distribution, inactivation, and excretion (generally, through respiration) rates of the CO as well as other factors known to those of skill in the art. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. Acute, sub-acute and chronic administration of CO are contemplated by the present invention, depending upon, e.g., the severity or persistence of NEC in the patient. CO can be delivered to the patient for a time (including indefinitely) sufficient to treat the condition and exert the intended pharmacological or biological effect.

The following are examples of some methods and devices that can be utilized to administer gaseous CO compositions to patients.

Ventilators

Medical grade CO (concentrations can vary) can be purchased mixed with air or another oxygen-containing gas in a standard tank of compressed gas (e.g., 21% $O_2$, 79% $N_2$). It is non-reactive, and the concentrations that are required for the methods of the present invention are well below the combustible range (10% in air). In a hospital setting, the gas presumably will be delivered to the bedside where it will be mixed with oxygen or house air in a blender to a desired concentration in ppm (parts per million). The patient will inhale the gas mixture through a ventilator, which will be set to a flow rate based on patient comfort and needs. This is determined by pulmonary graphics (i.e., respiratory rate, tidal volumes etc.). Fail-safe mechanism(s) to prevent the patient from unnecessarily receiving greater than desired amounts of CO can be designed into the delivery system. The patient's CO level can be monitored by studying (1) carboxyhemoglobin (COHb), which can be measured in venous blood, and (2) exhaled CO collected from a side port of the ventilator. CO exposure can be adjusted based upon the patient's health status and on the basis of the markers. If necessary, CO can be washed out of the patient by switching to 100% $O_2$ inhalation. CO is not metabolized; thus, whatever is inhaled will ultimately be exhaled except for a very small percentage that is converted to $CO_2$. CO can also be mixed with any level of $O_2$ to provide therapeutic delivery of CO without consequential hypoxic conditions.

Face Mask and Tent

A CO-containing gas mixture is prepared as above to allow passive inhalation by the patient using a facemask or tent. The concentration inhaled can be changed and can be washed out by simply switching over to 100% $O_2$. Monitoring of CO levels would occur at or near the mask or tent with a fail-safe mechanism that would prevent too high of a concentration of CO from being inhaled.

Portable Inhaler

Compressed CO can be packaged into a portable inhaler device and inhaled in a metered dose, for example, to permit intermittent treatment of a recipient who is not in a hospital setting. Different concentrations of CO could be packaged in the containers. The device could be as simple as a small tank (e.g., under 5 kg) of appropriately diluted CO with an on-off valve and a tube from which the patient takes a whiff of CO according to a standard regimen or as needed.

Intravenous Artificial Lung

An artificial lung (a catheter device for gas exchange in the blood) designed for $O_2$ delivery and $CO_2$ removal can be used for CO delivery. The catheter, when implanted, resides in one of the large veins and would be able to deliver CO at given concentrations either for systemic delivery or at a local site. The delivery can be a local delivery of a high concentration of CO for a short period of time at the site of the procedure, e.g., in proximity to the small intestine (this high concentration would rapidly be diluted out in the bloodstream), or a relatively longer exposure to a lower concentration of CO (see, e.g., Hattler et al., Artif. Organs 18(11):806-812 (1994); and Golob et al., ASAIO J., 47(5):432-437 (2001)).

Normobaric Chamber

In certain instances, it would be desirable to expose the whole patient to CO. The patient would be inside an airtight chamber that would be flooded with CO (at a level that does not endanger the patient, or at a level that poses an acceptable risk without the risk of bystanders being exposed. Upon completion of the exposure, the chamber could be flushed with air (e.g., 21% $O_2$, 79% $N_2$) and samples could be analyzed by CO analyzers to ensure no CO remains before allowing the patient to exit the exposure system.

Systemic Delivery of Liquid CO Compositions

The present invention further contemplates that liquid CO compositions can be created for systemic delivery to a patient, e.g., by infusion into a patient. For example, liquid CO compositions, such as CO-saturated Ringer's Solution, can be infused into a patient suffering from or at risk for NEC. Alternatively or in addition, CO-partially or completely saturated whole (or partial) blood can be infused into the patient. The present invention also contemplates that agents capable of delivering doses of CO gas or liquid can be utilized (e.g., CO releasing gums, creams, ointments or patches).

Topical Treatment of the Gastrointestinal Tract with Carbon Monoxide

Alternatively or in addition, CO compositions can be applied directly to the gastrointestinal tract, e.g., to the interior and/or exterior of the entire gastrointestinal tract, or to any portion thereof A gaseous composition can be directly applied to the gastrointestinal tract of a patient, e.g., a premature infant or newborn, by any method known in the art for insufflating gases into a patient. For example, gases, e.g., carbon dioxide, are often insufflated into the gastrointestinal tract and the abdominal cavity of patients to facilitate examination during endoscopic and laproscopic procedures, respectively (see, e.g., Oxford Textbook of Surgery, Morris and Malt, Eds., Oxford University Press (1994)). The skilled practitioner will appreciate that similar procedures could be used to administer CO compositions directly to the gastrointestinal tract of a patient. It is also contemplated that the present invention can be applied to help prevent NEC resulting from laproscopy and endoscopy, e.g., colonoscopy and oesophagogastroduodenoscopy.

Aqueous CO compositions can also be administered topically to the gastrointestinal tract of a patient. Aqueous forms of the compositions can be administered by any method known in the art for administering liquids to patients. As with gaseous compositions, aqueous compositions can be applied directly to the interior and/or exterior of the gastrointestinal tract. For example, the aqueous form can be administered orally, e.g., by causing the patient to ingest an encapsulated or unencapsulated dose of the aqueous CO composition. As another example, liquids, e.g., saline solutions containing dissolved CO, can be injected into the gastrointestinal tract and the abdominal cavity of patients during endoscopic and laproscopic procedures, respectively. Further, an in situ exposure can be carried out by flushing the gastrointestinal tract or a portion thereof with a liquid CO composition (see Oxford Textbook of Surgery, Morris and Malt, Eds., Oxford University Press (1994)).

Use of Hemoxygenase-1, Other Compounds, and Other Treatments for NEC

Also contemplated by the present invention is the induction or expression of hemeoxygenase-1 (HO-1) in conjunction with administration of CO. For example, HO-1 can be induced in a patient suffering from or at risk for NEC. As used herein, the term "induce(d)" means to cause increased production of a protein, e.g., HO-1, in isolated cells or the cells of a tissue, organ or animal using the cells' own endogenous (e.g., non-recombinant) gene that encodes the protein.

HO-1 can be induced in a patient by any method known in the art. For example, production of HO-1 can be induced by hemin, by iron protoporphyrin, or by cobalt protoporphyrin. A variety of non-heme agents including heavy metals, cytokines, hormones, NO, $COCl_2$, endotoxin and heat shock are also strong inducers of HO-1 expression (Choi et al., Am. J. Respir. Cell Mol. Biol. 15:9-19, 1996; Maines, Annu. Rev. Pharmacol. Toxicol. 37:517-554, 1997; and Tenhunen et al., J. Lab. Clin. Med. 75:410-421, 1970). HO-1 is also highly induced by a variety of agents causing oxidative stress, including hydrogen peroxide, glutathione depletors, UV irradiation, endotoxin and hyperoxia (Choi et al., Am. J. Respir. Cell Mol. Biol. 15:9-19, 1996; Maines, Annu. Rev. Pharmacol. Toxicol. 37:517-554, 1997; and Keyse et al., Proc. Natl. Acad. Sci. USA 86:99-103, 1989). A "pharmaceutical composition comprising an inducer of HO-1" means a pharmaceutical composition containing any agent capable of inducing HO-1 in a patient, e.g., any of the agents described above, e.g., hemin, iron protoporphyrin, and/or cobalt protoporphyrin.

HO-1 expression in a cell can be increased via gene transfer. As used herein, the term "express(ed)" means to cause increased production of a protein, e.g., HO-1 or ferritin, in isolated cells or the cells of a tissue, organ or animal using an exogenously administered gene (e.g., a recombinant gene). The HO-1 or ferritin is preferably of the same species (e.g., human, mouse, rat, etc.) as the recipient, in order to minimize any immune reaction. Expression could be driven by a constitutive promoter (e.g., cytomegalovirus promoters) or a tissue-specific promoter (e.g., milk whey promoter for mammary cells or albumin promoter for liver cells). An appropriate gene therapy vector (e.g., retrovirus, adenovirus, adeno associated virus (AAV), pox (e.g., vaccinia) virus, human immunodeficiency virus (HIV), the minute virus of mice, hepatitis B virus, influenza virus, Herpes Simplex Virus-1, and lentivirus) encoding HO-1 or ferritin would be administered to a patient suffering from or at risk for NEC, by mouth, by inhalation, or by injection into the intestinal wall, intestinal lumen, or abdominal cavity. Similarly, plasmid vectors encoding HO-1 or apoferritin can be administered, e.g., as naked DNA, in liposomes, or in microparticles.

Further, exogenous HO-1 protein can be directly administered to a patient by any method known in the art. Exogenous HO-1 can be directly administered in addition, or as an alternative, to the induction or expression of HO-1 in the patient as described above. The HO-1 protein can be delivered to a patient, for example, in liposomes, and/or as a fusion protein, e.g., as a TAT-fusion protein (see, e.g., Becker-Hapak et al., Methods 24:247-256, 2001).

Alternatively or in addition, any of the products of metabolism by HO-1, e.g., bilirubin, biliverdin, iron, and/or ferritin, can be administered to a patient in conjunction with CO in order to prevent or treat NEC. Further, the present invention contemplates that iron-binding molecules other than ferritin, e.g., desferoxamine (DFO), iron dextran, and/or apoferritin, can be administered to the patient. Further still, the present invention contemplates that enzymes (e.g., biliverdin reductase) that catalyze the breakdown any of these products can be inhibited to create/enhance the desired effect. Any of the above can be administered, e.g., orally, intravenously, intraperitoneally, or by direct administration to the inside or outside of the bowel.

The present invention contemplates that compounds that release CO into the body after administration of the compound (e.g., CO-releasing compounds, e.g., photoactivatable CO-releasing compounds), e.g., dimanganese decacarbonyl, tricarbonyldichlororuthenium (II) dimer, and methylene chloride (e.g., at a dose of between 400 to 600 mg/kg, e.g., about 500 mg/kg), can also be used in the methods of the present invention, as can carboxyhemoglobin and CO-donating hemoglobin substitutes.

The above can be administered to a patient in any way, e.g., by oral, intraperitoneal, intravenous, or intraarterial administration. Any of the above compounds can be administered to the patient locally and/or systemically, and in any combination.

The present invention further contemplates treating NEC by administering CO to the patient in combination with any other known methods or compounds for treating NEC, e.g., cessation or reduction of the rate of feeding by mouth, e.g., for at least 1 day, e.g., at least 2, 3, 5, or 10 days, or more); administering intravenous hydration and/or nutrition, nasogastric decompression, or antimicrobial agents to the patient; surgical intervention; and/or draining the patient's peritoneal cavity. Surgical interventions include, e.g., resecting the affected portion of the bowel. Also contemplated is preventive treatment of patients at risk for NEC by administering CO to the patient in combination with any other known methods for preventing NEC, e.g., changing the patient's diet.

The invention is illustrated in part by the following examples, which are not to be taken as limiting the invention in any way.

EXAMPLE 1

CO Attenuates the Development of NEC

Collection of Human Intestinal Specimens

Human intestinal specimens were collected and snap frozen at the time of operation.

Animal Model of Necrotizing Enterocolitis

Pregnant time-dated Sprague-Dawley rats were induced at term using subcutaneous injection of Pitocin (1 U). Immediately after birth (day zero), the neonates were weighed and randomized into two main groups. Animals were either left with their mothers and thus breast-fed, or separated from their mothers, housed in an incubator (Ohio Medical Products, Madison, Wis.), gavage fed with a special rodent formula two times daily, and subjected to 10 minutes of hypoxia (5% $O_2$, 95% $N_2$; PraxAir, Pittsburgh, Pa.) prior to each feeding. The formula consisted of 15 g Similac® 60/40 (Ross Pediatrics, Colombus, Ohio) in 75 mL of Esbilac® canine milk replacement (Pet-Ag Inc., Hampshire, Ill.). Rats from each group were further randomized to receive no additional treatment or one-hour per day CO treatment (250 parts per million; ppm, days 1-3). CO was delivered as described below. The neonatal rats were sacrificed on day four. The intestines were inspected for gross necrotic changes and pneumatosis intestinalis. The last 2 cm of terminal ileum was harvested for morphological studies, and mucosal scrapings were collected for detection of protein.

CO Exposure

Animals were exposed to CO at a concentration of 250 ppm. Briefly, 1% CO in air was mixed with air (21% oxygen) in a stainless steel mixing cylinder and then directed into a 3.70 $ft^3$ glass exposure chamber at a flow rate of 12 L/min. A CO analyzer (Interscan, Chatsworth, Calif.) was used to measure CO levels continuously in the chamber. CO concentrations were maintained at 250 ppm at all times. Rats were placed in the exposure chamber as required.

Morphological Studies

Intestinal specimens were harvested as described above. Hematoxylin and eosin (H&E) slides were prepared as per standard protocol and examined by light microscopy. The presence of morphological changes in the intestinal epithelium, including separation of the villous core, submucosal edema, and epithelial sloughing, were determined by a pathologist in a blinded fashion.

Serum Cytokine Determination

Serum was collected for determination of rat TNF-α and IL-1β levels using Quantikine® ELISA (R&D systems, Minneapolis, Minn.) per the manufacturer's instructions.

Cell Culture

The rat small-intestinal epithelial cell line IEC-6 was obtained from the American Type Culture Collection (Manassas, Va.). Cells were grown in Dulbecco's modified Eagle's medium with 4.5 g/L glucose (Bio-Whittaker, Walkersville, Md.) supplemented with 5% fetal bovine serum, 0.02 mM glutamine (Gibco, Grand Island, N.Y.), 0.1 U/mL insulin, and 100 U/mL penicillin/100 µg/mL streptomycin at 37° C. and 10% $CO_2$. Cells from passages 3 through 20 were used for experiments.

Viability

Cell viability was determined by measuring ATP levels (CellTiter-Glo™; Promega) as per the manufacturer's protocol.

Western Blot Analysis

IEC-6 cells or ileal mucosal scrapings were collected in lysis buffer containing 20 mmol/L Tris with 100 µmol/L phenylmethylsulfonylfluoride (Sigma), 1 µmol/L leupeptin (Sigma), and 1 µmol/L sodium orthovanadate (Sigma). Protein was quantified by bicinchoninic acid (BCA) protein assay (Pierce, Rockford, Ill.). Lysates (30 µg) were subjected to sodium dodecylsulfate-polyacrylamide gel electrophoresis.

Reporter Assay pGL3/2 rat iNOS promoter-luciferase reporter was constructed as described in Beck et al., FEBS Lett 435:35-38 (1998). IEC-6 cells grown in 35 mm wells were transfected with 4 µL Lipofectamine2000® (Invitrogen), 0.15 µg pGL3/2 DNA and 0.5 µg pIEP-LacZ DNA, which was used as a control for transfection efficiency. Twenty-four hours following transfection, cells were treated for 6 hours, then lysates were collected and a luciferase assay (Promega) was performed with a luminometer (Berthold, Germany).

Nitrite Determination

Nitrite ($NO_2^-$) was measured in the culture medium using the Griess method.

Statistical Analysis

Results are expressed as mean±SEM. Differences among groups were analyzed with one-way analysis of variance with Student-Newman-Keuls post-hoc test for all pairwise comparisons (SigmaStat; SPSS, Chicago, Ill.). Statistical significance was assumed when P was less than 0.05.

Intestinal HO-1 Protein is Increased in NEC

Human intestinal specimens from patients with NEC and control intestinal specimens from patients with non-inflammatory conditions were analyzed for expression of HO-1. Whole cell lysates from NEC specimens demonstrated increased expression of HO-1 compared to controls (FIG. 1A).

Figure 1B:
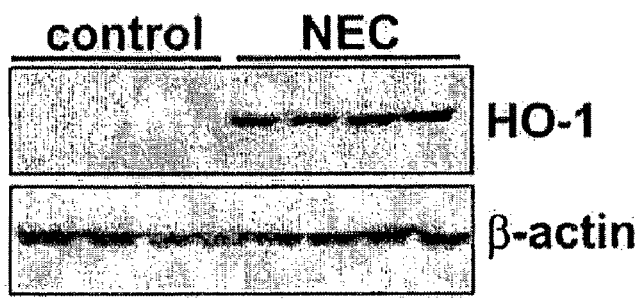
FIG. 1B is a picture of a Western blot illustrating that ileal HO-1 protein is increased at day four in neonatal rats subjected to intermittent hypoxia and formula feeding (NEC) as compared to breast fed control rats (control) (n=4).
Figures 2A, 2B, 2C, 2D:
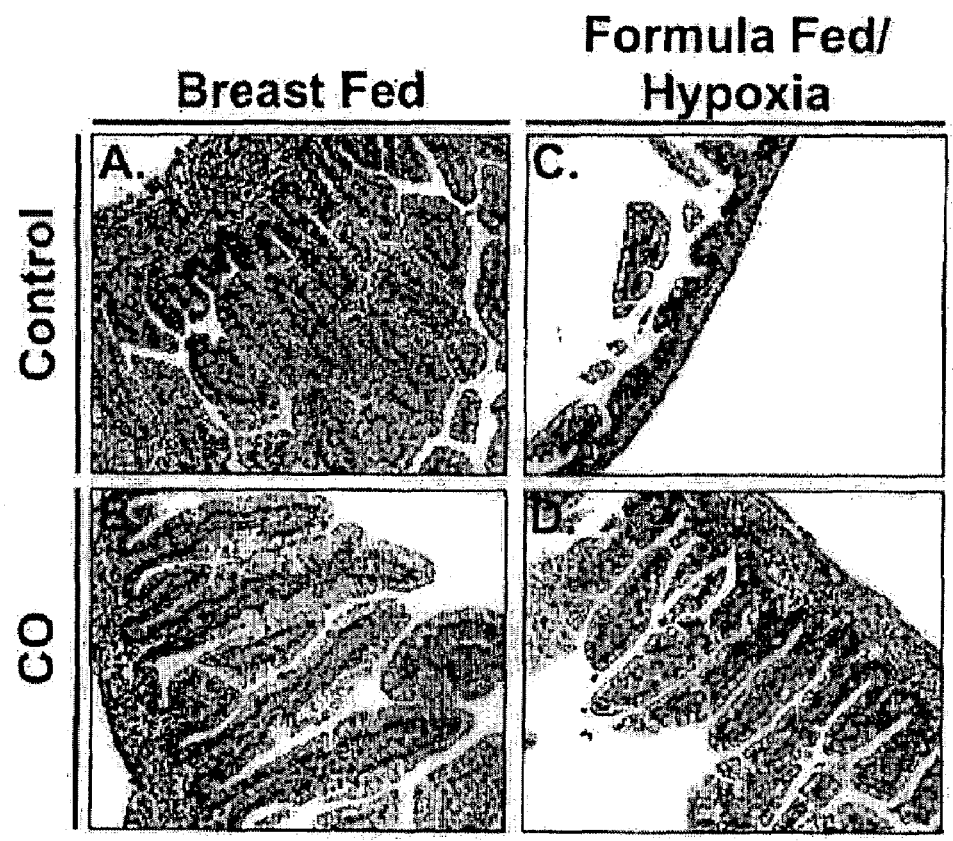
FIG. 2A is a photomicrograph (40× magnification) of a hematoxylin and eosin-stained ileal whole mount illustrating the effect of breast feeding on a neonatal rat. The sample was obtained on day four.
FIG. 2B is a photomicrograph (40× magnification) of a hematoxylin and eosin-stained ileal whole mount illustrating the effect of breast feeding and CO exposure on a neonatal rat. The sample was obtained on day four.
FIG. 2C is a photomicrograph (40× magnification) of a hematoxylin and eosin-stained ileal whole mount illustrating the effect of formula feeding plus hypoxia exposure on a neonatal rat. The sample was obtained on day four. Architectural changes including villous atrophy and cellular vacuolization can be observed.
FIG. 2D is a photomicrograph (40× magnification) of a hematoxylin and eosin-stained ileal whole mount illustrating the effect of formula feeding, plus hypoxia exposure and CO exposure on a neonatal rat. Fewer architectural changes occur as compared to the sample shown in FIG. 2C. The sample was obtained on day four.
Figures 3A, 3B, 3C, 3D:
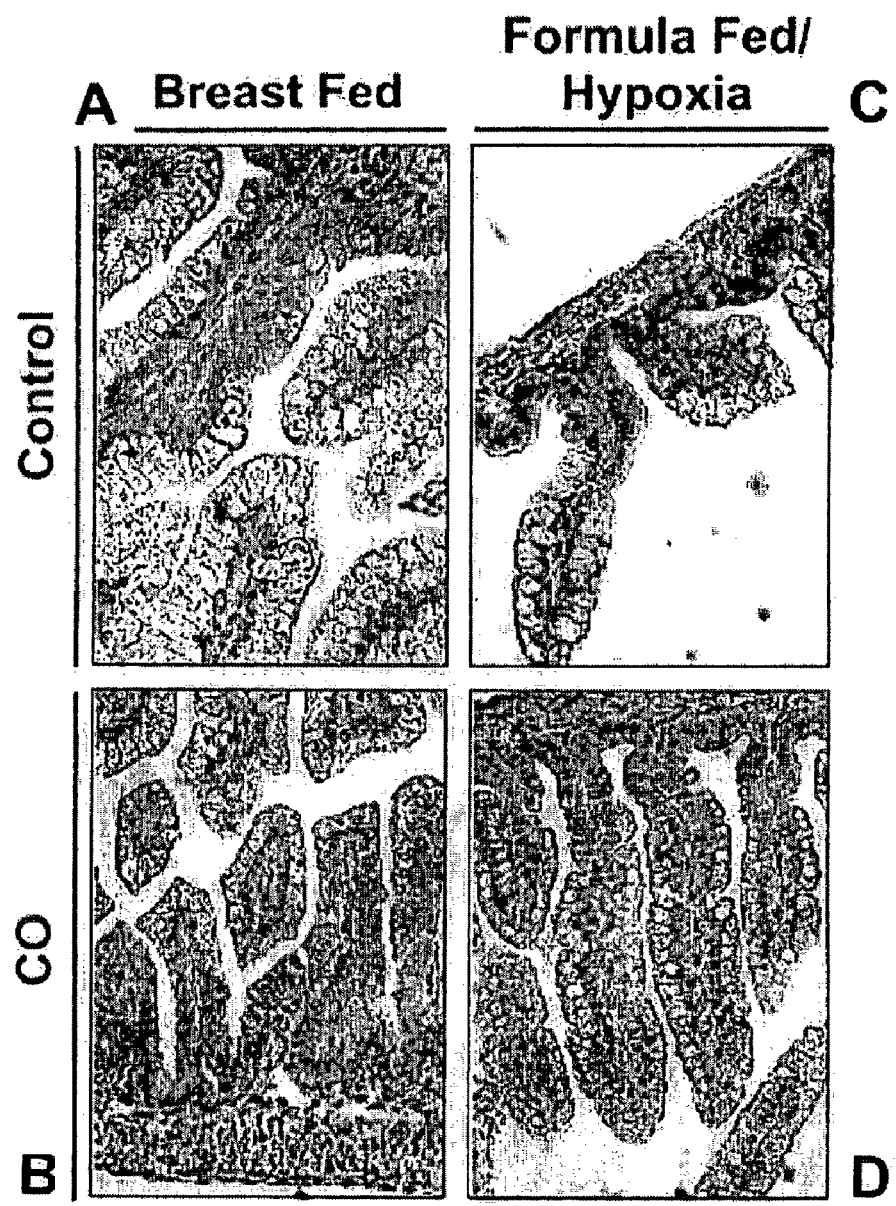
FIG. 3A is a photomicrograph (60× magnification) of a terminal deoxynucleotidyl transferase mediated dUTP nick end labeling (TUNEL)-stained ileal whole mount illustrating the effect of breast feeding on a neonatal rat. The sample was obtained on day four.
FIG. 3B is a photomicrograph (60× magnification) of a TUNEL-stained ileal whole mount illustrating the effect of breast feeding and CO exposure on a neonatal rat. The sample was obtained on day four.
FIG. 3C is a photomicrograph (60× magnification) of a TUNEL-stained ileal whole mount illustrating the effect of formula feeding plus hypoxia exposure on a neonatal rat. The sample was obtained on day four. Ileum from hypoxia/formula-fed treated rats exhibits increased TUNEL staining compared to that from breast fed animals.
FIG. 3D is a photomicrograph (60× magnification) of a TUNEL-stained ileal whole mount illustrating the effect of formula feeding plus hypoxia exposure, and CO exposure on a neonatal rat. The sample was obtained on day four. A decrease in TUNEL positive cells can be observed.

To determine whether intestinal HO-1 protein levels would be increased in a model of experimental NEC, neonatal rats were randomized to breast feed ad libitum or to be subjected to intermittent hypoxia and formula fed (H/F) as described above. All animals were sacrificed on day 4 of life and terminal ileal mucosa were collected and analyzed by Western blotting. HO-1 protein expression was increased in the H/F group compared to breast fed control animals (FIG. 1B). This is consistent with previous findings in the intestine and other organs that illustrate upregulation of HO-1 following a variety of injuries.

CO Protects Against the Development of NEC

Neonatal rats from breast fed and H/F groups were randomized to receive either one-hour doses of CO (250 ppm) per day on days 1, 2, and 3, or no additional therapy. All animals were sacrificed on day 4 of life. Gross pathological characteristics including pneumatosis intestinalis and necrosis (see Table 1, below) as well as histological changes consistent with experimental NEC were identified in the H/F group compared to breast fed controls (FIGS. 2A, 2B, 2C, and 2D). CO treatment had no effect on gross or microscopic evaluation of breast fed animals and significantly protected against the development of experimental NEC in rats in the H/F group. TUNEL staining for cell death, which was increased in the H/F group, was diminished by CO treatment (FIGS. 3A, 3B, 3C, and 3D).

TABLE 1

Pathological changes from neonatal rat ileum on day 4 of life.

|  | Breast-fed | Breast-fed + CO | Formula-Fed/Hypoxia | Formula-Fed/Hypoxia + CO |
|---|---|---|---|---|
| Total number (n) | 7 | 7 | 8 | 8 |
| Gross Changes (n) |  |  |  |  |
| Bowel wall necrosis | 0 | 0 | 5 | 2 |
| Pneumatosis intestinalis | 0 | 0 | 5 | 1 |
| Microscopic Changes (n) |  |  |  |  |
| Villous atrophy | 0 | 0 | 7 | 2 |
| Vacuolization | 0 | 1 | 6 | 3 |
| Stromal neutrophils | 0 | 0 | 6 | 1 |

CO Decreases Systemic Markers of Inflammation.

Figure 4A:
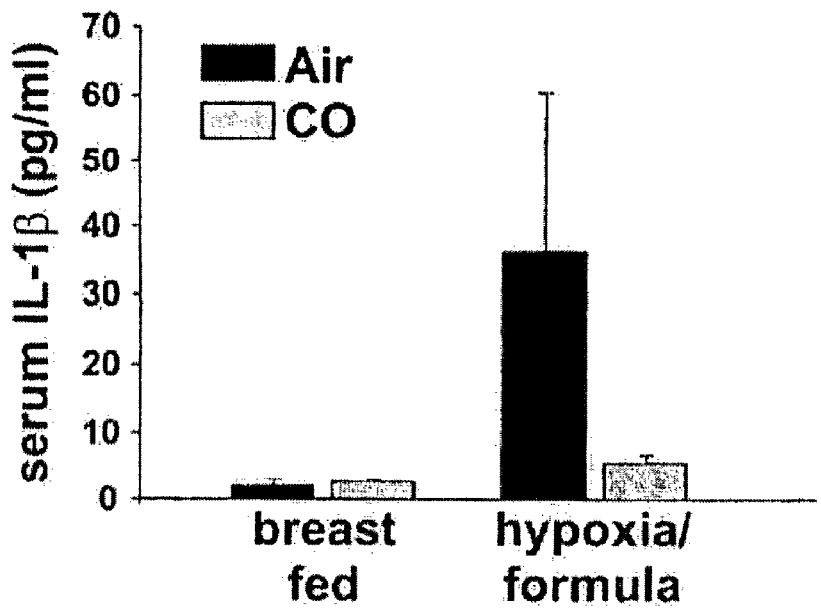
FIG. 4A is a bar graph illustrating that CO treatment prevents an increase in the serum IL-1β level in hypoxia-exposed plus formula-fed neonatal rats as compared to controls ($P<0.05$). The data was generated using an ELISA assay. Black bars=air-exposed rats; gray bars=CO exposed rats.
Figure 4B:
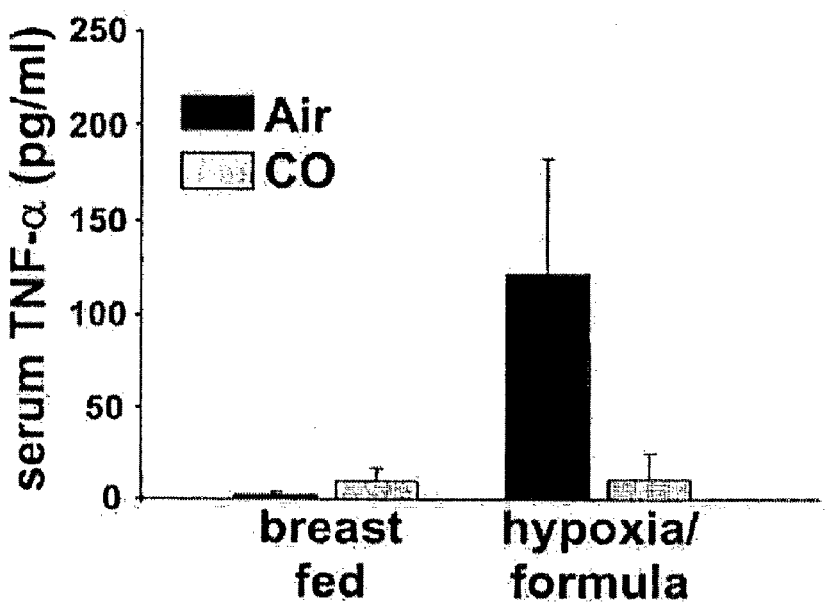
FIG. 4B is a bar graph illustrating that CO treatment prevents an increase in the serum TNF-α level in hypoxia-exposed and formula-fed neonatal rats as compared to controls ($P<0.05$). The data was generated using an ELISA assay. Black bars=air-exposed rats; gray bars=CO-exposed rats.

At the time of sacrifice, serum was collected for measurement of TNF-α and IL-1β levels as systemic markers of tissue inflammation. Levels of both TNF-α and IL-1β were increased by 33.2 and 18.5 fold in the H/F group compared to breast fed controls (FIGS. 4A and 4B; P<0.05). CO significantly attenuated these increases, resulting in only 3 and 2.5 fold increases in TNF-α and IL-1β, respectively (P<0.05). These findings demonstrate that exogenous CO can abrogate some of the systemic consequences in this animal model.

CO Decreases Local Intestinal Markers of Inflammation.

Figure 5:
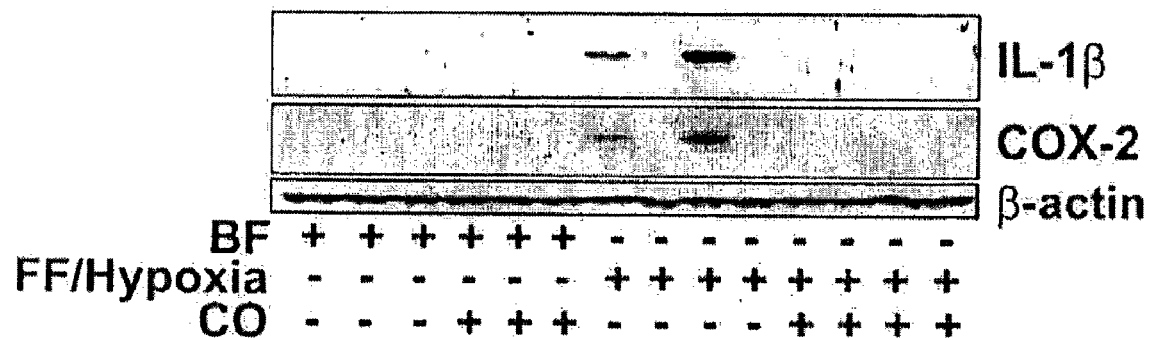
FIG. 5 is a picture of a Western blot illustrating that CO treatment decreases ileal expression of COX-2 and IL-1β in hypoxia-exposed and formula-fed neonatal rats, as compared to controls. The presence (+) or absence (−) of each treatment (breast feeding (BF), formula-feeding plus hypoxia exposure (FF/Hypoxia) and CO exposure (CO)) is indicated beneath each lane of the Western blot. Blot demonstrates 3-4 animals per group and is representative of all animals in the study.

Assays were performed for cyclooxygenase-2 (COX-2) and interleukin-1β (IL-1β), both of which are markers of intestinal inflammation and have been demonstrated to be associated with NEC. Ileal mucosal protein lysates were evaluated by Western blot analysis for COX-2 and IL-1β. In this study H/F was associated with an increase in ileal COX-2 and IL-1β protein levels in approximately half of the animals (FIG. 5). Consistent with the protective effects on histology and serum cytokines, CO-treatment decreased expression of both of these proteins. CO also decreased expression of ileal HO-1 in this model (data not shown), which likely represents a decrease in intestinal injury and the compensatory changes that occur in response to the injury.

Figure 6:
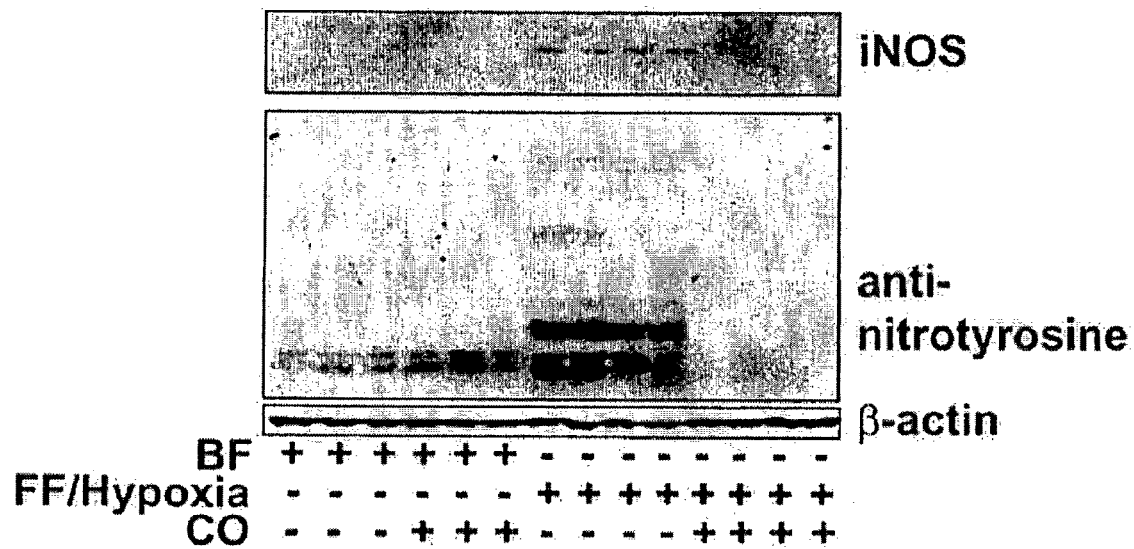
FIG. 6 is a picture of a Western blot illustrating that exposure to CO abrogates experimental NEC-induced ileal iNOS expression and protein nitration in neonatal rats. The presence (+) or absence (−) of each treatment (breast feeding (BF), formula-feeding plus hypoxia exposure (FF/Hypoxia) and CO exposure (CO) is indicated beneath each lane of the Western blot.

CO Inhibits Generation of Intestinal Inducible Nitric Oxide Synthase (iNOS)

iNOS is increased in human intestinal specimens from neonates with NEC as well as in the intestines of rats in experimental models of NEC. Induction of iNOS and NO generation are believed to contribute directly to tissue damage via formation of reactive nitrogen species. Western blot analysis of ileal mucosal samples in this study demonstrate that H/F results in increased levels of iNOS and protein nitration (FIG. 6). Nitration or nitrotyrosine formation is thought to be caused by peroxynitrite, the toxic product of the interaction of NO and superoxide. Both iNOS protein and nitrosotyrosines were markedly decreased in animals treated with CO, suggesting that CO may be protective in the intestines by decreasing/preventing the generation of NO.

HO-1/CO Inhibits IEC-6 Cell Death

Figure 7:
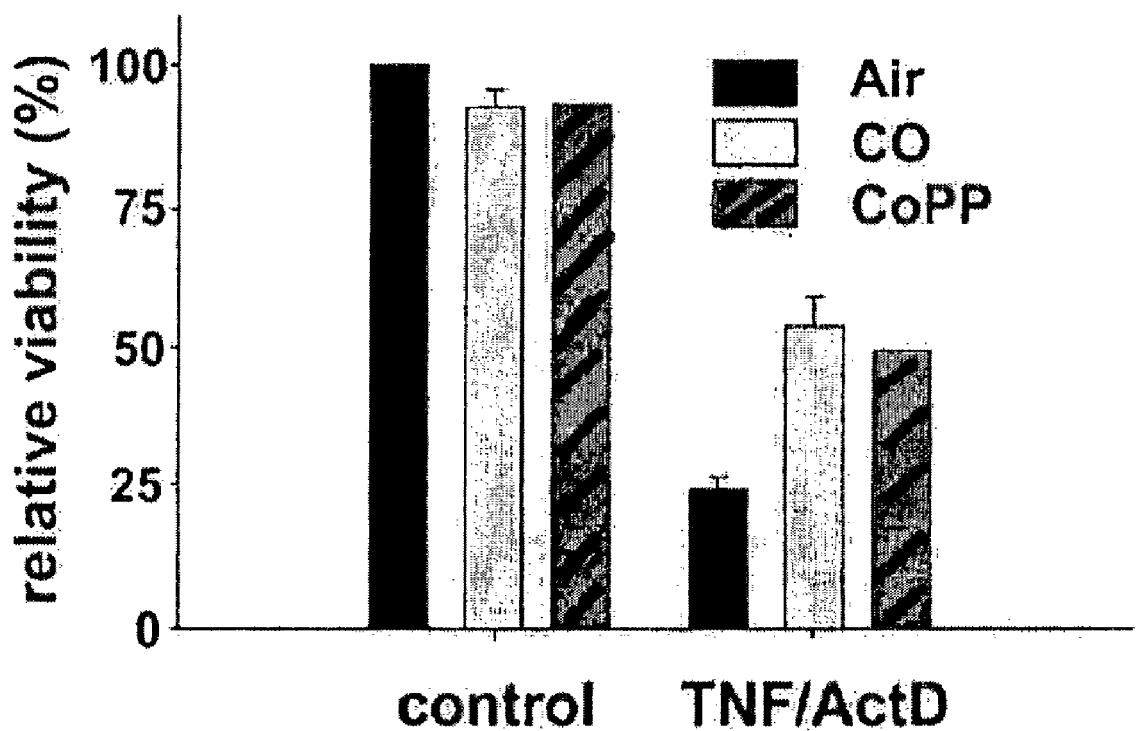
FIG. 7 is a bar graph illustrating that CO exposure and induction of HO-1 decreases TNF-α/Actinomycin D (TNF/ActD)-induced IEC-6 cell death. Viability of TNF-α (TNF; 10 ng/ml)/Actinomycin D (ActD; 200 ng/ml)-treated IEC-6 cells was assayed after 18 hours by measuring cellular ATP content. CO treatment (CO; gray bars; 250 ppm) was initiated 1 hour prior to administration of TNF-α/ActD and maintained throughout the duration of the experiment. Cross-hatched bars=cells exposed to cobalt protoporphyrin (CoPP) 16 hours prior to exposure to TNF-α/ActD. Black bars=air exposed cells. Both CO and CoPP significantly decreased TNF-α/ActD-induced IEC-6 cell death ($P<0.05$). Results are mean±standard error of 3 independent studies performed in triplicate.

To determine whether HO-1 or CO inhibits cell death in vitro, the rat intestinal epithelial cell line IEC-6 was utilized. Cell death was induced by treating these cells with TNF-α (10 ng/ml) plus actinomycin D (ActD; 200 ng/ml). Cell viability was analyzed by crystal violet staining of adherent cells and assessment of cellular ATP content. TNF-α/ActD decreased IEC-6 cell viability to 24±2.1% that of untreated controls (FIG. 7; P<0.05). CO significantly inhibited the TNF-α/ActD-induced cell death resulting in 54±5.6% viability compared to untreated controls (P<0.05). CO alone had no measurable effect on viability of IEC-6 cells in vitro. Induction of HO-1 by CoPP had similar protective effects.

CO Prevents iNOS Upregulation/NO Generation

Figures 8A, 8B, 8C, 8D:
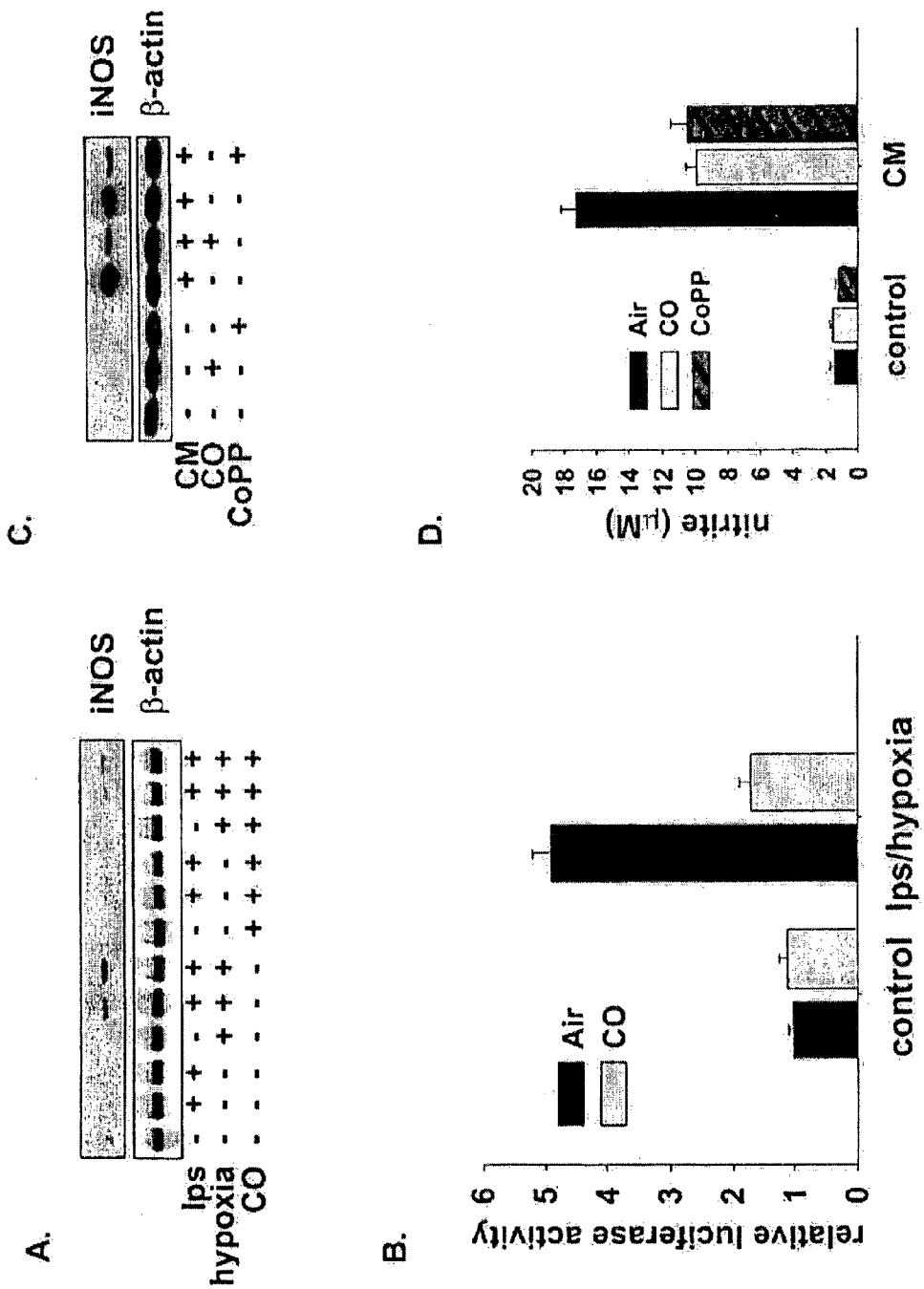
FIG. 8A is a picture of a Western blot illustrating (at 24 hours) that iNOS protein expression is inhibited in lipopolysaccharide (LPS) and/or hypoxia (1% oxygen) treated IEC-6 cells. CO treatment (250 ppm) was initiated 1 hour before the addition of LPS/hypoxia and maintained throughout the experiment. The combination of LPS (10 or 100 ng/ml) plus hypoxia increased iNOS protein expression, an effect that was inhibited by CO. The presence (+) or absence (−) of each treatment (lipopolysaccharide (lps), hypoxia exposure (hypoxia) and CO exposure (CO)) is indicated beneath each lane of the Western blot.
FIG. 8B is a bar graph illustrating that rat iNOS promoter activity in LPS (100 ng/ml)/hypoxia (1% oxygen; lps/hypoxia)-treated IEC-6 cells is limited by exposure to CO. Cells were assayed for luciferase activity. The combination of LPS plus hypoxia resulted in a 4.9±0.3 fold increase in transcriptional activation of the iNOS promoter (P<0.05). CO limited this transcriptional activation to a 1.7±0.2 fold increase (P<0.05). Results are mean±standard error of 3 independent studies performed in triplicate.
FIG. 8C is a picture of a Western blot illustrating that cytokine-induced iNOS protein expression is inhibited in IEC-6 cells by induction of HO-1 or treatment with CO. IEC-6 cells were treated with a cytokine mixture (CM) containing TNF-$\alpha$ (10 ng/ml), IL-1$\beta$ (500 U/ml), and IFN-$\gamma$ (1000 U/ml) for 24 hours. CO treatment (250 ppm) was initiated 1 hour prior to administration of CM and maintained throughout the duration of the experiment. Cobalt protoporphyrin (CoPP) was administered 16 hours prior to CM treatment. CM increased IEC-6 cell iNOS protein. Both CO and CoPP inhibited cytokine-induced increase in iNOS protein. The presence (+) or absence (−) of each treatment (cytokine mixture (CM), CO exposure (CO), and cobalt protoporphyrin exposure (CoPP)) is indicated beneath each lane of the Western blot.
FIG. 8D is a bar graph illustrating that the nitrite levels in supernatantants of IEC-6 cells that are exposed to CM and either CO or CoPP are lower than those of IEC-6 cells exposed to CM and air (as determined by Griess assay). Cytokine stimulation increased nitrite to 17.2±0.9 µM compared to 1.4±0.3 µM in unstimulated controls (P<0.01). CO and CoPP significantly inhibited this cytokine effect resulting in nitrite levels of 9.8±0.7 and 10.4±1.0, respectively (P<0.05 compared to CM-stimulated cells). Black bars=air exposed cells; gray bars=CO exposed cells; and cross-hatched bars=CoPP exposed cells.

Whether CO can inhibit the upregulation of iNOS intestinal epithelial cells in vitro was investigated. The effects of LPS and/or 1% oxygen (hypoxia) were investigated on iNOS protein by Western blotting. These studies demonstrate that LPS/hypoxia increased iNOS protein, which is an effect that was inhibited by CO (FIG. 8A). The effects of CO on transcriptional activation of the rat iNOS promoter was tested in IEC-6 cells stimulated with LPS and hypoxia (FIG. 8B). The combination of LPS plus hypoxia resulted in a 4.9±0.3 fold increase in transcriptional activation of the iNOS promoter utilizing a luciferase assay (P<0.05). CO limited this transcriptional activation to only a 1.7±0.2 fold increase(P<0.05). Additionally, the effect of CO on NO generation by IEC-6 cells was assayed by measuring nitrite. IEC-6 cells were stimulated with a cytokine mixture (TNF-α, IL-1β, Interferon-γ) that is known to upregulate iNOS. Cytokine stimulation increased iNOS protein (FIG. 8C) as well as nitrite to 17.2±0.9 µM compared to 1.4±0.3 µM in unstimulated controls (P<0.0; FIG. 8D). CO and CoPP significantly inhibited this cytokine effect resulting in nitrite levels of 9.8±0.7 and 10.4±1.0, respectively (P<0.05).

The data presented above indicate that HO-1 is upregulated in intestinal specimens from human neonates with NEC as well as in the ileal mucosa of neonatal rats in a model of experimental NEC. One-hour per day of exogenous CO delivery prevented the development of NEC. This was associated with a decrease in systemic inflammation as assayed by serum TNF-α and IL-1β, and local inflammation as assayed by ileal mucosal expression of IL-1β and COX-2. The development of NEC was also associated with increased ileal mucosal iNOS expression and protein nitration. CO therapy attenuated the increase in iNOS and nitrosative stress. In vitro, induction of HO-1 or CO is protective against TNF-α/ActD-induced cell death in IEC-6 cells. Additionally in vitro, CO prevented iNOS induction and NO generation.

HO-1 and its catalytic by-products, including CO, likely play a defensive role following intestinal injury. The data presented above demonstrate that levels of HO-1 protein are increased in the ileal mucosa of animals with NEC, which is consistent with previous studies demonstrating increased intestinal HO-1 in models of ischemia/reperfusion and hemorrhagic shock. Induction of HO-1, by pre-conditioning or pharmacologically, is cytoprotective following intestinal transplantation and ischemia/reperfusion. CO treatment, which is protective against the development of NEC, also prevented the upregulation of HO-1. This inhibition of HO-1 expression may be due to a direct negative feedback loop; however, this is likely secondary to the protection against intestinal injury with subsequent upregulation of HO-1.

One hour of CO inhalation therapy (250 ppm) per day was sufficient to prevent the development of NEC. The protective effects of CO in this animal model of NEC are likely to be multifactorial. The data presented above demonstrate that CO administration causes a decrease in intestinal apoptosis as assayed by TUNEL staining in vivo and amelioration of TNF-α/ActD-induced IEC-6 cell death in vitro. CO therapy was also associated with decreased elaboration of both systemic and local inflammatory mediators.

iNOS/NO are associated with mucosal damage and gut barrier failure in inflammatory bowel disease, experimental ileitis, endotoxic shock and NEC. The data presented above show that CO decreases the upregulation of iNOS in vitro and in vivo, in addition to decreasing nitrosotyrosine formation in vivo. Peroxynitrite, which is believed to be the reactive nitrogen species responsible for enterocyte toxicity and apoptosis, reacts with proteins to result in nitration of tyrosine residues. This species is thought to be formed by the interaction of NO and superoxide. CO-mediated enterocyte protection may be mediated by inhibition of iNOS protein upregulation, decreasing subsequent NO and peroxynitrite generation.

Prevention of the development of NEC by CO may involve maintained gastrointestinal motility and prevention of inappropriate bacterial colonization. Altered intestinal colonization is known to contribute to the development of NEC.

In conclusion, the present example demonstrates that one-hour of CO therapy per day protected formula-fed/hypoxic neonatal rats from the development of experimental NEC. The mechanism appears to involve the inhibition of iNOS expression and protein nitration.

EXAMPLE 2

Protocol for the Treatment of NEC

The following example illustrates protocols for use in treating a patient suffering from or at risk for NEC. The example also illustrates protocols for treating patients before, during, and/or after surgical procedures, e.g., a surgical procedure to treat NEC, e.g., a surgery in which a portion of the bowel is resected. Skilled practitioners will appreciate that any protocol described herein can be adapted based on a patient's individual needs, and can be adapted to be used in conjunction with any other treatment for NEC.

Treatment of a patient with CO can begin on the day the patient is diagnosed as suffering from NEC or any condition associated with NEC, or as having any risk factor associated with an increased likelihood that the patient will develop NEC. Patients can inhale CO at concentrations ranging from 10 ppm to 1000 ppm, e.g., about 100 ppm to about 800 ppm, about 150 ppm to about 600 ppm, or about 200 ppm to about 500 ppm. Preferred concentrations include, e.g., about 30 ppm, 50 ppm, 75 ppm, 100 ppm, 125 ppm, 200 ppm, 250 ppm, 500 ppm, 750 ppm, or about 1000 ppm. CO can be administered to the patient intermittently or continuously. CO can be administered for about 1, 2, 4, 6, 8, 10, 12, 14, 18, or 20 days, or greater than 20 days, e.g., 1 2, 3, 5, or 6 months, or until the patient no longer exhibits symptoms of NEC, or until the patient is diagnosed as no longer being at risk for NEC. In a given day, CO can be administered continuously for the entire day, or intermittently, e.g., a single whiff of CO per day (where a high concentration is used), or for up to 23 hours per day, e.g., up to 20, 15, 12, 10, 6, 3, or 2 hours per day, or up to 1 hour per day.

With regard to the administration of CO in conjunction with surgical procedures to treat NEC, CO can be administered systemically or locally to a patient prior to, during, and/or after a surgical procedure is performed. Patients can inhale CO at concentrations ranging from 10 ppm to 1000 ppm, e.g., about 100 ppm to about 800 ppm, about 150 ppm to about 600 ppm, or about 200 ppm to about 500 ppm. Preferred concentrations include, e.g., about 30 ppm, 50 ppm, 75 ppm, 100 ppm, 125 ppm, 200 ppm, 250 ppm, 500 ppm, 750 ppm, or about 1000 ppm. CO can be administered to the patient intermittently or continuously, for about 1, 2, 4, 6, 8, 10, 12, 14, 18, or 20 days, or greater than 20 days, before the procedure. Alternatively or in addition, CO can be administered to the patient during the procedure, e.g., by inhalation and/or topical administration. Alternatively or in addition, CO can be administered to the patient after the procedure, e.g., starting immediately after completion of the procedure, and continuing for about 1, 2, 3, 5, 7, or 10 hours, or about 1, 2, 5, 8, 10, 20, 30, 50, or 60 days, indefinitely, or until the patient no longer suffers from, or is at risk for, NEC after the completion of the procedure.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating necrotizing enterocolitis in a patient, comprising:
   identifying a patient suffering from or at risk for necrotizing enterocolitis; and
   administering to the patient a gaseous composition comprising carbon monoxide in an amount sufficient to treat necrotizing enterocolitis in the patient, wherein the carbon monoxide is present in the composition at concentration of 10 ppm to about 3000 ppm, and wherein the composition is administered by inhalation.

2. The method of claim 1, wherein the patient is an infant.

3. The method of claim 2, wherein the patient is a premature infant.

4. The method of claim 1, wherein the patient exhibits low birth weight.

5. The method of claim 1, wherein the patient exhibits hypoxia.

6. The method of claim 1, wherein the patient exhibits hypothermia.

7. The method of claim 1, wherein the patient exhibits hypotension.

8. The method of claim 1, wherein the patient exhibits hyperviscosity of the blood.

9. The method of claim 1, wherein the patient exhibits acidosis.

10. The method of claim 1, wherein the patient has received an exchange transfusion.

11. The method of claim 1, wherein the patient has received at least one hyperosmolar feed.

12. The method of claim 1, wherein the patient has received a packed cell transfusion.

13. The method of claim 1, wherein the patient has received an overdosage of calcium antagonists.

14. The method of claim 1, wherein the patient suffers from mesenteric ischaemia.

15. The method of claim 1, wherein the patient suffers from a bacterial infection of the bowel wall.

16. The method of claim 1, wherein the patient has undergone surgery.

17. The method of claim 1, wherein the patient is about to undergo surgery.

18. The method of claim 1, wherein the patient is undergoing surgery.

19. The method of claim 1, further comprising administering to the patient a treatment selected from the group consisting of: intravenous nutrition; intravenous hydration; antimicrobial agents; performing nasogastric decompression on the patient, performing surgery on the patient; and draining the patient peritoneal cavity.

20. The method of claim 1, wherein the carbon monoxide is present in the composition at concentration of 10 ppm to about 2,500 ppm.

21. The method of claim 1, wherein the carbon monoxide is present in the composition at concentration of 10 ppm to about 1,000 ppm.

22. The method of claim 1, wherein the carbon monoxide is present in the composition at concentration of about 50 ppm to about 3,000 ppm.

23. The method of claim 1, wherein the carbon monoxide is present in the composition at concentration of about 100 ppm to about 3,000 ppm.

24. The method of claim 1, wherein the carbon monoxide is present in the composition at concentration of about 50 ppm to about 3,000 ppm.

25. The method of claim 1, wherein the carbon monoxide is present in the composition at concentration of about 500 ppm to about 3,000 ppm.

26. The method of claim 1, wherein the composition comprises carbon monoxide gas at a concentration of about 200 ppm to about 500 ppm.

27. The method of claim 1, wherein the composition comprises carbon monoxide gas at a concentration of about 150 ppm to about 600 ppm.

28. The method of claim 1, wherein the composition comprises carbon monoxide gas at a concentration of about 100 ppm to about 800 ppm.

29. A method of treating necrotizing enterocolitis in a patient, comprising:
   (a) identifying a patient suffering from necrotizing enterocolitis;
   (b) performing surgery on the patient to resect an affected portion of the patient's bowel; and
   (c) administering to the patient after (a) and before, during, or after (b), a gaseous composition comprising carbon monoxide in an amount sufficient to treat necrotizing enterocolitis in the patient, wherein the carbon monoxide is at a concentration of 10 ppm to about 3000 ppm, and wherein the gaseous composition and is administered to the patient via inhalation.

30. The method of claim 29, wherein the composition comprises carbon monoxide gas at a concentration of 10 ppm to about 2,500 ppm.

31. The method of claim 29, wherein the composition comprises carbon monoxide gas at a concentration of 10 ppm to about 1,000 ppm.

32. The method of claim 29, wherein the carbon monoxide is present in the composition at concentration of about 50 ppm to about 3,000 ppm.

33. The method of claim 29, wherein the carbon monoxide is present in the composition at concentration of about 100 ppm to about 3,000 ppm.

34. The method of claim 29, wherein the carbon monoxide is present in the composition at concentration of about 50 ppm to about 3,000 ppm.

35. The method of claim 29, wherein the carbon monoxide is present in the composition at concentration of about 500 ppm to about 3,000 ppm.

36. The method of claim 29, wherein the composition comprises carbon monoxide gas at a concentration of about 200 ppm to about 500 ppm.

37. The method of claim 29, wherein the composition comprises carbon monoxide gas at a concentration of about 150 ppm to about 600 ppm.

38. The method of claim 29, wherein the composition comprises carbon monoxide gas at a concentration of about 100 ppm to about 800 ppm.

39. A method of treating necrotizing enterocolitis in a patient, comprising:
- (a) identifying a patient suffering from or at risk for necrotizing enterocolitis;
- (b) providing a vessel containing a pressurized gas comprising carbon monoxide gas;
- (c) releasing the pressurized gas from the vessel, to form an atmosphere comprising carbon monoxide gas at a concentration of 10 ppm to about 3000 ppm; and
- (d) exposing the patient to the atmosphere, wherein the amount of carbon monoxide in the atmosphere is sufficient to treat necrotizing enterocolitis in the patient and wherein the patient inhales the atmosphere.

\* \* \* \* \*

UNITED STATES PATENT AND TRADEMARK OFFICE
CERTIFICATE OF CORRECTION

PATENT NO. : 7,981,448 B2
APPLICATION NO. : 10/413817
DATED : July 19, 2011
INVENTOR(S) : Leo E. Otterbein Page 1 of 1

It is certified that error appears in the above-identified patent and that said Letters Patent is hereby corrected as shown below:

First page, column 2, line 2, other publications, delete "carveric dononrs," and insert -- cadaveric donors, --.

Column 18, line 3, in claim 19, replace "patient" with -- patient's --.

Column 18, line 42, in claim 29, after "composition" delete "and".

Signed and Sealed this
Twenty-fifth Day of October, 2011

David J. Kappos
*Director of the United States Patent and Trademark Office*

UNITED STATES PATENT AND TRADEMARK OFFICE
CERTIFICATE OF CORRECTION

| | | Page 1 of 1 |
|---|---|---|
| PATENT NO. | : 7,981,448 B2 | |
| APPLICATION NO. | : 10/413817 | |
| DATED | : July 19, 2011 | |
| INVENTOR(S) | : Leo E. Otterbein | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 350 days.

Signed and Sealed this
Twenty-ninth Day of May, 2012

David J. Kappos
*Director of the United States Patent and Trademark Office*